United States Patent [19]

Glass et al.

[11] Patent Number: 5,773,009
[45] Date of Patent: Jun. 30, 1998

[54] ROTAVIRUS STRAIN G9P11

[75] Inventors: Roger I. Glass; John R. Gentsch, both of Atlanta, Ga.; M. K. Bhan; Bimal K. Das, both of New Delhi, India

[73] Assignee: The United States of America as represented by the Department of Health and Human Services, Washington, D.C.

[21] Appl. No.: 802,141

[22] Filed: Feb. 19, 1997

Related U.S. Application Data

[63] Continuation of Ser. No. 231,041, Apr. 15, 1994, abandoned.
[51] Int. Cl.$^6$ .............................. A61K 39/15; C12N 7/00; C12N 7/01; C12N 15/63
[52] U.S. Cl. .................................... 424/215.1; 435/235.1; 435/320.1
[58] Field of Search .............................. 424/215.1, 205.1; 435/320.1, 235.1, 172.1, 172.3

[56] References Cited

U.S. PATENT DOCUMENTS 5,474,773  12/1995  Ward ..................................... 424/184.1

OTHER PUBLICATIONS

Bhan et al. *J. Infect. Diseases* 168:282–287, 1993.
Gentsch et al. *Virol.* 194:424–430, 1993.
Das et al. *Virol.* 197:99–107, 1993.
Das et al. *Virol.* 194(1):374–379, 1993.
Gentsch et al. *J. Clin. Microbiol.* 30(6):1365–1373, 1992.
Bhan et al. *Plediatr. Infect. Dis. J.* 7(5):320–323, 1988.
Jayashree et al. *J. Infect. Dis.* 158(5):1117–1120, 1988.
Glass et al. *Virol.* 141:292–298, 1985.
Hardy et al, Virology, 1992, vol. 191:pp. 291–300.

*Primary Examiner*—Nancy Degen
*Assistant Examiner*—Terry A. McKelvey
*Attorney, Agent, or Firm*—Fitch, Even, Tabin & Flannery

[57] ABSTRACT

Provided is an isolated rotavirus of the strain G9P11, an isolated nucleic acid encoding the rotavirus of strain G9P11 and a purified antigen specific for the rotavirus. An isolated nucleic acid encoding the antigen of the rotavirus is also provided, as is an isolated nucleic acid that selectively hybridizes under high stringency conditions with the nucleic acid encoding te virus. A purified antibody which selectively binds the virus of strain G9P11 is provided. The G9P11 rotavirus in a pharmaceutically acceptable carrier for administration in an immunization protocol is provided. Also provided is an isolated rotavirus of strain G9P11, wherein the G9 gene is substituted. Further provided is an isolated rotavirus of strain G9P11, wherein the P11 gene is substituted.

4 Claims, 1 Drawing Sheet

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1061 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 49..1029

( x i ) SEQUENCE DESCRIPTION: SEQ ID NO:1:

```
GGCTTTAAAA GAGAGAATTT CCGTTTGGCT AGCGGTTAGC TCCTTTTA ATG TAT GGT          57
                                                    Met Tyr Gly
                                                      1

ATT GAA TAT ACC ACA GTT CTA ACC TTT TTG ATA TCA ATC ATT TTA TTG          105
Ile Glu Tyr Thr Thr Val Leu Thr Phe Leu Ile Ser Ile Ile Leu Leu
      5                   10                  15

AAT TAT ATA TTG AAA TCA GTA ACT AGT GCA ATG GAC TTT ATA ATT TAT          153
Asn Tyr Ile Leu Lys Ser Val Thr Ser Ala Met Asp Phe Ile Ile Tyr
 20                  25                  30                  35

AGG TTT CTT TTA ATT ATT GTC GTT GTG TCA CCA TTC GTC AAA ACA CAA          201
Arg Phe Leu Leu Ile Ile Val Val Val Ser Pro Phe Val Lys Thr Gln
                 40                  45                  50

AAT TAT GGA ATT AAC GTA CCG ATC ACT GGT TCC ATG GAT ACA GCA TAT          249
Asn Tyr Gly Ile Asn Val Pro Ile Thr Gly Ser Met Asp Thr Ala Tyr
             55                  60                  65

ACA AAT TCA TCA CAG CAA GAG ACA TTT TTA ACT TCA ACG TTG TGC TTA          297
Thr Asn Ser Ser Gln Gln Glu Thr Phe Leu Thr Ser Thr Leu Cys Leu
         70                  75                  80

TAT TAT CCT ATT GAA GCA TCA ACT CAA ATT GGG GAC ACA GAA TGG AAA          345
Tyr Tyr Pro Ile Glu Ala Ser Thr Gln Ile Gly Asp Thr Glu Trp Lys
     85                  90                  95

GGT ACT TTG TCT CAG TTA TTC TTA ACT AAA GGA TGG CCA ACT GGA TCA          393
Gly Thr Leu Ser Gln Leu Phe Leu Thr Lys Gly Trp Pro Thr Gly Ser
100                 105                 110                 115

GTT TAT TTT AAA GAA TAT ACC GAT ATC GCT TCA TTT TCA ATC GAT CCA          441
Val Tyr Phe Lys Glu Tyr Thr Asp Ile Ala Ser Phe Ser Ile Asp Pro
                120                 125                 130

CAA TTT TAT TGC GAT TAT AAC GTT GTG TTA GTG AAA TAT AAT TCA ACA          489
Gln Phe Tyr Cys Asp Tyr Asn Val Val Leu Val Lys Tyr Asn Ser Thr
            135                 140                 145

TTA GAG TTA GAT ATG TCT GAA CTA GCT GAT TTG ATT TTA AAT GAA TGG          537
Leu Glu Leu Asp Met Ser Glu Leu Ala Asp Leu Ile Leu Asn Glu Trp
        150                 155                 160

TTA TGT AAT CCG ATG GAT ATA GCA TTA TAT TAT TAT CAG CAA ACA AAT          585
Leu Cys Asn Pro Met Asp Ile Ala Leu Tyr Tyr Tyr Gln Gln Thr Asn
    165                 170                 175

GAA GCG AAC AAA TGG ATA TCA ATG GGA CAA TCT TGT ACA ATA AAA GTA          633
Glu Ala Asn Lys Trp Ile Ser Met Gly Gln Ser Cys Thr Ile Lys Val
180                 185                 190                 195

TGT CCA TTG AAT ACA CAA ACT TTA GGA ATA GGA TGT ACA ACT ACA AAT          681
Cys Pro Leu Asn Thr Gln Thr Leu Gly Ile Gly Cys Thr Thr Thr Asn
                200                 205                 210
```

| | | | | | | | | | | | | | | | | |
|---|---|---|---|---|---|---|---|---|---|---|---|---|---|---|---|---|
| ACG | GCG | ACA | TTT | GAA | GAG | GTA | GCG | ACG | AAC | GAA | AAA | TTA | GTA | ATA | ACC | 729 |
| Thr | Ala | Thr | Phe<br>215 | Glu | Glu | Val | Ala | Thr<br>220 | Asn | Glu | Lys | Leu | Val<br>225 | Ile | Thr | |
| GAT | GTT | GTT | GAT | GGT | GTA | AAT | CAT | AAA | CTT | GAT | GTA | ACT | ACC | AAC | ACC | 777 |
| Asp | Val | Val<br>230 | Asp | Gly | Val | Asn | His<br>235 | Lys | Leu | Asp | Val | Thr<br>240 | Thr | Asn | Thr | |
| TGC | ACA | ATT | AGA | AAT | TGT | AGA | AAG | TTA | GGA | CCA | AGA | GAG | AAT | GTG | GCA | 825 |
| Cys | Thr<br>245 | Ile | Arg | Asn | Cys | Arg<br>250 | Lys | Leu | Gly | Pro | Arg<br>255 | Glu | Asn | Val | Ala | |
| AAG | TTA | CAA | GTT | GGC | GGC | TCA | GAA | GTG | CTA | GAC | ATT | ACA | GCA | GAT | CCA | 873 |
| Lys<br>260 | Leu | Gln | Val | Gly | Gly<br>265 | Ser | Glu | Val | Leu | Asp<br>270 | Ile | Thr | Ala | Asp | Pro<br>275 | |
| ACC | ACT | ACA | CCA | CAA | ACC | GAG | CGC | ATG | ATG | CAA | ATA | AAT | TGG | AAG | AAA | 921 |
| Thr | Thr | Thr | Pro | Gln<br>280 | Thr | Glu | Arg | Met | Met<br>285 | Gln | Ile | Asn | Trp | Lys<br>290 | Lys | |
| TGG | TGG | CAA | GTT | TTT | TAT | ACA | GTA | GTA | GAT | TAT | ATT | AAT | CAA | ATT | GTG | 969 |
| Trp | Trp | Gln | Val<br>295 | Phe | Tyr | Thr | Val | Val<br>300 | Asp | Tyr | Ile | Asn | Gln<br>305 | Ile | Val | |
| CAA | GTT | ATG | TCC | AAA | AGA | TCA | CGA | TCG | TTC | AAT | TCA | GCA | GCT | TTT | TAT | 1017 |
| Gln | Val | Met<br>310 | Ser | Lys | Arg | Ser | Arg<br>315 | Ser | Phe | Asn | Ser | Ala<br>320 | Ala | Phe | Tyr | |
| TAT | AGA | ATC | TGATATATCT | TAGATTAGAA | CTGGTCGATG | TGACC | | | | | | | | | | 1061 |
| Tyr | Arg | Ile<br>325 | | | | | | | | | | | | | | |

( 2 ) INFORMATION FOR SEQ ID NO:2:

( i ) SEQUENCE CHARACTERISTICS:
        ( A ) LENGTH: 326 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Tyr | Gly | Ile | Glu<br>5 | Tyr | Thr | Thr | Val | Leu<br>10 | Thr | Phe | Leu | Ile | Ser<br>15 | Ile |
| Ile | Leu | Leu | Asn<br>20 | Tyr | Ile | Leu | Lys<br>25 | Ser | Val | Thr | Ser | Ala<br>30 | Met | Asp | Phe |
| Ile | Ile | Tyr<br>35 | Arg | Phe | Leu | Leu | Ile<br>40 | Ile | Val | Val | Val | Ser<br>45 | Pro | Phe | Val |
| Lys | Thr<br>50 | Gln | Asn | Tyr | Gly | Ile<br>55 | Asn | Val | Pro | Ile | Thr<br>60 | Gly | Ser | Met | Asp |
| Thr<br>65 | Ala | Tyr | Thr | Asn | Ser<br>70 | Ser | Gln | Gln | Glu | Thr<br>75 | Phe | Leu | Thr | Ser | Thr<br>80 |
| Leu | Cys | Leu | Tyr | Tyr<br>85 | Pro | Ile | Glu | Ala | Ser<br>90 | Thr | Gln | Ile | Gly | Asp<br>95 | Thr |
| Glu | Trp | Lys | Gly<br>100 | Thr | Leu | Ser | Gln | Leu<br>105 | Phe | Leu | Thr | Lys | Gly<br>110 | Trp | Pro |
| Thr | Gly | Ser<br>115 | Val | Tyr | Phe | Lys | Glu<br>120 | Tyr | Thr | Asp | Ile | Ala<br>125 | Ser | Phe | Ser |
| Ile | Asp<br>130 | Pro | Gln | Phe | Tyr | Cys<br>135 | Asp | Tyr | Asn | Val | Val<br>140 | Leu | Val | Lys | Tyr |
| Asn<br>145 | Ser | Thr | Leu | Glu | Leu<br>150 | Asp | Met | Ser | Glu | Leu<br>155 | Ala | Asp | Leu | Ile | Leu<br>160 |
| Asn | Glu | Trp | Leu | Cys<br>165 | Asn | Pro | Met | Asp | Ile<br>170 | Ala | Leu | Tyr | Tyr | Tyr<br>175 | Gln |
| Gln | Thr | Asn | Glu<br>180 | Ala | Asn | Lys | Trp | Ile<br>185 | Ser | Met | Gly | Gln | Ser<br>190 | Cys | Thr |

| | | | | | | | | | | | | | | |
|---|---|---|---|---|---|---|---|---|---|---|---|---|---|---|
| Ile | Lys | Val<br>195 | Cys | Pro | Leu | Asn | Thr<br>200 | Gln | Thr | Leu | Gly<br>205 | Ile | Gly | Cys | Thr |
| Thr | Thr<br>210 | Asn | Thr | Ala | Thr | Phe<br>215 | Glu | Glu | Val | Ala | Thr<br>220 | Asn | Glu | Lys | Leu |
| Val<br>225 | Ile | Thr | Asp | Val | Val<br>230 | Asp | Gly | Val | Asn | His<br>235 | Lys | Leu | Asp | Val | Thr<br>240 |
| Thr | Asn | Thr | Cys | Thr<br>245 | Ile | Arg | Asn | Cys | Arg<br>250 | Lys | Leu | Gly | Pro | Arg<br>255 | Glu |
| Asn | Val | Ala | Lys<br>260 | Leu | Gln | Val | Gly | Gly<br>265 | Ser | Glu | Val | Leu | Asp<br>270 | Ile | Thr |
| Ala | Asp | Pro<br>275 | Thr | Thr | Thr | Pro | Gln<br>280 | Thr | Glu | Arg | Met | Met<br>285 | Gln | Ile | Asn |
| Trp | Lys<br>290 | Lys | Trp | Trp | Gln | Val<br>295 | Phe | Tyr | Thr | Val | Val<br>300 | Asp | Tyr | Ile | Asn |
| Gln<br>305 | Ile | Val | Gln | Val | Met<br>310 | Ser | Lys | Arg | Ser | Arg<br>315 | Ser | Phe | Asn | Ser | Ala<br>320 |
| Ala | Phe | Tyr | Tyr | Arg<br>325 | Ile | | | | | | | | | | |

(2) INFORMATION FOR SEQ ID NO:3:

(i) SEQUENCE CHARACTERISTICS:
        (A) LENGTH: 2352 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 11..2329

(xi) SEQUENCE DESCRIPTION: SEQ ID NO:3:

| | | | | | | | | | | | | | | |
|---|---|---|---|---|---|---|---|---|---|---|---|---|---|---|
| GGCTTTTATA | ATG | CGT | TCG | CTA | ATA | TAC | AGA | CAG | CTA | CTT | TAT | AAC | TCA | 49 |
| | Met<br>1 | Arg | Ser | Leu | Ile<br>5 | Tyr | Arg | Gln | Leu | Leu<br>10 | Tyr | Asn | Ser | |
| TAT | TCA | GTA | GAT | TTA | TCA | GAT | GAA | ATA | ACT | AAT | ATA | GGT | GCA | GAA | AAG | 97 |
| Tyr | Ser<br>15 | Val | Asp | Leu | Ser | Asp<br>20 | Glu | Ile | Thr | Asn | Ile<br>25 | Gly | Ala | Glu | Lys | |
| AAA | GAG | AAT | GTG | ACT | GTA | CAG | ATT | GGT | GAG | TTC | GCT | CAA | AGT | CAA | TAC | 145 |
| Lys<br>30 | Glu | Asn | Val | Thr | Val<br>35 | Gln | Ile | Gly | Glu | Phe<br>40 | Ala | Gln | Ser | Gln | Tyr<br>45 | |
| GCA | CCA | GTT | TCG | TGG | GGA | TCA | GGA | GAG | ACG | TTA | AGC | GGA | AAT | GTT | GAA | 193 |
| Ala | Pro | Val | Ser | Trp<br>50 | Gly | Ser | Gly | Glu | Thr<br>55 | Leu | Ser | Gly | Asn | Val<br>60 | Glu | |
| GAG | CAA | CCT | TTA | GAC | GGG | CCA | TAT | ACA | CCA | GAT | AAG | TCA | AAT | TTG | CCG | 241 |
| Glu | Gln | Pro | Leu<br>65 | Asp | Gly | Pro | Tyr | Thr<br>70 | Pro | Asp | Lys | Ser | Asn<br>75 | Leu | Pro | |
| TCT | AAC | TAT | TGG | TAT | TTA | ATC | AAT | CCA | TCA | AAT | GAT | GGC | GTG | GTG | TTC | 289 |
| Ser | Asn | Tyr<br>80 | Trp | Tyr | Leu | Ile | Asn<br>85 | Pro | Ser | Asn | Asp | Gly<br>90 | Val | Val | Phe | |
| TCG | GTA | ACG | GAT | AAC | AGT | ACG | CTT | TGG | ATG | TTT | ACT | TAT | TTA | GTC | TTA | 337 |
| Ser | Val<br>95 | Thr | Asp | Asn | Ser | Thr<br>100 | Leu | Trp | Met | Phe | Thr<br>105 | Tyr | Leu | Val | Leu | |
| CCA | AAT | ACA | GCT | CAG | ACT | AGT | GTC | GTA | GTA | AAT | GTA | ATG | AAT | GAG | ACA | 385 |
| Pro | Asn | Thr<br>110 | Ala | Gln | Thr | Ser<br>115 | Val | Val | Val | Asn | Val<br>120 | Met | Asn | Glu | Thr<br>125 | |
| GTG | AAT | ATA | TCA | ATA | GAC | AAC | TCA | GGT | TCG | GCA | TAT | AAA | TTT | GTG | GAT | 433 |
| Val | Asn | Ile | Ser | Ile<br>130 | Asp | Asn | Ser | Gly | Ser<br>135 | Ala | Tyr | Lys | Phe | Val<br>140 | Asp | |

| | | | | | | | | | | | | | | | | |
|---|---|---|---|---|---|---|---|---|---|---|---|---|---|---|---|---|
|TAC|TTT|AAG|ACT|AGT|TCC|GCA|CAA|GCG|TAT|AGG|TCA|AGG|AAC|TTT|CTG|481|
|Tyr|Phe|Lys|Thr 145|Ser|Ser|Ala|Gln 150|Ala|Tyr|Arg|Ser|Arg 155|Asn|Phe|Leu| |

|ATT|ACT|GCA|CAC|AGA|TTG|CAA|GCT|TAC|AAG|AGA|GAT|GGA|GAT|GGA|AAT|529|
|Ile|Thr|Ala|His 160|Arg|Leu|Gln|Ala 165|Tyr|Lys|Arg|Asp|Gly 170|Asp|Gly|Asn| |

|ATA|TCA|AAT|TAT|TGG|GGT|TCG|GAT|GCA|TAC|GGT|GAT|CTG|AGA|GTT|GGA|577|
|Ile|Ser|Asn 175|Tyr|Trp|Gly|Ser|Asp 180|Ala|Tyr|Gly|Asp|Leu 185|Arg|Val|Gly| |

|ACA|TAT|TTT|AAT|CCA|GTG|CCA|AAT|GCA|GTG|ATT|AAT|CTA|AAT|GCA|GAT|625|
|Thr 190|Tyr|Phe|Asn|Pro|Val 195|Pro|Asn|Ala|Val|Ile 200|Asn|Leu|Asn|Ala|Asp 205| |

|TTT|TAC|GTT|ATA|CCA|GAT|TCG|CAA|CAA|GAG|ATG|TGT|ACA|GAG|TAT|ATA|673|
|Phe|Tyr|Val|Ile|Pro 210|Asp|Ser|Gln|Gln|Glu 215|Met|Cys|Thr|Glu|Tyr 220|Ile| |

|AGG|AGA|GGA|TTG|CCA|GCC|ATA|CAA|ACT|ACA|ACT|TAT|GTG|ACA|CCA|ATC|721|
|Arg|Arg|Gly|Leu 225|Pro|Ala|Ile|Gln|Thr 230|Thr|Thr|Tyr|Val|Thr 235|Pro|Ile| |

|AGT|TAT|GCT|GTT|AGA|AGT|CAA|AGA|ATT|GCG|AGA|CCG|AAT|GAA|GAC|ATA|769|
|Ser|Tyr|Ala 240|Val|Arg|Ser|Gln|Arg 245|Ile|Ala|Arg|Pro|Asn 250|Glu|Asp|Ile| |

|ACC|ATA|TCA|AAA|GCA|TCA|CTA|TGG|AAA|GAG|GTT|CAA|TAT|AAT|AGA|GAC|817|
|Thr|Ile 255|Ser|Lys|Ala|Ser|Leu 260|Trp|Lys|Glu|Val|Gln 265|Tyr|Asn|Arg|Asp| |

|ATT|GTG|ATA|AGA|TTT|GTG|TTT|GCA|AAT|AAT|ATA|ATC|AAA|GCA|GGT|GGA|865|
|Ile 270|Val|Ile|Arg|Phe|Val 275|Phe|Ala|Asn|Asn|Ile 280|Ile|Lys|Ala|Gly|Gly 285| |

|CTT|GGT|TAT|AAA|TGG|TCA|GAG|ATA|TCA|TAT|AAG|GCT|AAT|AAT|TAT|CAA|913|
|Leu|Gly|Tyr|Lys|Trp 290|Ser|Glu|Ile|Ser|Tyr 295|Lys|Ala|Asn|Asn|Tyr 300|Gln| |

|TAT|ACA|TAT|ATG|AGG|GAT|GGC|ATA|GAA|GTT|GTT|GCT|CAT|ACT|ACT|GTT|961|
|Tyr|Thr|Tyr|Met 305|Arg|Asp|Gly|Ile|Glu 310|Val|Val|Ala|His|Thr 315|Thr|Val| |

|TCA|GTG|AAC|GGT|GTT|AGT|GTG|TAT|GAT|TAT|AAC|ACT|GGG|TCG|TTA|CCA|1009|
|Ser|Val|Asn 320|Gly|Val|Ser|Val|Tyr 325|Asp|Tyr|Asn|Thr|Gly 330|Ser|Leu|Pro| |

|ACT|GAT|TTC|ACG|ATC|CGA|AAT|TAC|GAC|GTT|TTG|AAA|GAA|AGT|TCG|TTC|1057|
|Thr|Asp 335|Phe|Thr|Ile|Arg|Asn 340|Tyr|Asp|Val|Leu|Lys 345|Glu|Ser|Ser|Phe| |

|GTA|TAC|GTT|GAT|TAT|TGG|GAC|GAT|TCA|CAG|GCT|TTT|AGA|AAT|ATG|GTA|1105|
|Val 350|Tyr|Val|Asp|Tyr|Trp 355|Asp|Asp|Ser|Gln|Ala 360|Phe|Arg|Asn|Met|Val 365| |

|TAT|GTG|CGG|TCG|CTG|AAT|GCA|GAA|TTA|AAT|CAA|GTG|CAA|TGT|GTA|GGA|1153|
|Tyr|Val|Arg|Ser|Leu 370|Asn|Ala|Glu|Leu|Asn 375|Gln|Val|Gln|Cys|Val 380|Gly| |

|GGT|CAT|TAC|TCG|TTC|GCG|TTG|CCT|GTT|GGC|TCA|TGG|CCG|GTG|ATG|CAA|1201|
|Gly|His|Tyr|Ser 385|Phe|Ala|Leu|Pro|Val 390|Gly|Ser|Trp|Pro|Val 395|Met|Gln| |

|GGA|GGG|AGT|GTG|GTT|CTA|ACA|TTT|GAT|GGT|GTA|ACG|TTA|TCA|ACA|CAG|1249|
|Gly|Gly|Ser|Val 400|Val|Leu|Thr|Phe|Asp 405|Gly|Val|Thr|Leu|Ser 410|Thr|Gln| |

|TTT|ACT|GAC|TAT|GTG|TCG|TTG|AAC|TCA|TTA|AGG|TTC|AGA|TTC|AGA|TGT|1297|
|Phe|Thr|Asp 415|Tyr|Val|Ser|Leu|Asn 420|Ser|Leu|Arg|Phe|Arg 425|Phe|Arg|Cys| |

|GCG|GTG|AGT|GAA|CCT|CCG|TTC|AGG|GTT|ACC|GGT|ACG|AGA|ATA|TCA|AAT|1345|
|Ala|Val|Ser|Glu 430|Pro|Pro|Phe|Arg|Val 435|Thr|Gly|Thr|Arg|Ile 440|Ser|Asn 445| |

|TTG|TAT|GGC|CTG|CCA|GCC|GCT|AAC|CCA|ATG|GGA|GAC|CAA|CAA|TAT|TAT|1393|
|Leu|Tyr|Gly|Leu|Pro 450|Ala|Ala|Asn|Pro|Met 455|Gly|Asp|Gln|Gln|Tyr 460|Tyr| |

| | | | | | | | | | | | | | | | | |
|---|---|---|---|---|---|---|---|---|---|---|---|---|---|---|---|---|
| GAA | GCA | TCA | GGT | AGG | TTC | TCG | TTG | ATT | TCG | TTA | GTG | CCT | AGT | AAT | GAT | 1441 |
| Glu | Ala | Ser | Gly | Arg | Phe | Ser | Leu | Ile | Ser | Leu | Val | Pro | Ser | Asn | Asp | |
| | | | 465 | | | | 470 | | | | | 475 | | | | |
| GAC | TAT | CAA | ACT | CCA | ATT | GCA | AAT | TCA | GTC | ACT | GTA | AGA | CAG | GAT | CTA | 1489 |
| Asp | Tyr | Gln | Thr | Pro | Ile | Ala | Asn | Ser | Val | Thr | Val | Arg | Gln | Asp | Leu | |
| | 480 | | | | | 485 | | | | | | 490 | | | | |
| GAG | AGA | CAG | CTA | GAT | GAA | ATG | AGG | AGA | GAA | TTC | AAT | GAA | CTA | TCA | GCT | 1537 |
| Glu | Arg | Gln | Leu | Asp | Glu | Met | Arg | Arg | Glu | Phe | Asn | Glu | Leu | Ser | Ala | |
| 495 | | | | | 500 | | | | | 505 | | | | | | |
| AAT | ATA | GCT | TTG | TCA | CAG | TTA | ATA | GAT | TTA | GCA | CTA | TTG | CCA | CTT | GAT | 1585 |
| Asn | Ile | Ala | Leu | Ser | Gln | Leu | Ile | Asp | Leu | Ala | Leu | Leu | Pro | Leu | Asp | |
| 510 | | | | | 515 | | | | | 520 | | | | | 525 | |
| ATG | TTC | TCA | ATG | TTC | AGC | GGA | ATA | CGA | AGT | ACC | ATT | GAA | GCA | GCA | AAA | 1633 |
| Met | Phe | Ser | Met | Phe | Ser | Gly | Ile | Arg | Ser | Thr | Ile | Glu | Ala | Ala | Lys | |
| | | | | 530 | | | | | 535 | | | | | 540 | | |
| AAC | TTC | GCG | ACG | TCG | GTG | ATG | AAG | AAG | TTT | AGA | AAG | TCA | AAT | TTG | GCG | 1681 |
| Asn | Phe | Ala | Thr | Ser | Val | Met | Lys | Lys | Phe | Arg | Lys | Ser | Asn | Leu | Ala | |
| | | | 545 | | | | 550 | | | | | 555 | | | | |
| AAA | AGT | GTT | AAT | AGT | TTG | ACT | GAT | GCA | ATA | ACG | GAT | GCC | GCT | GGC | TCA | 1729 |
| Lys | Ser | Val | Asn | Ser | Leu | Thr | Asp | Ala | Ile | Thr | Asp | Ala | Ala | Gly | Ser | |
| | | 560 | | | | | 565 | | | | | 570 | | | | |
| ATT | TCT | AGG | TCG | TCA | ACA | CTG | CGA | TCA | GCT | AAC | AGC | GCT | GTT | TCA | GTA | 1777 |
| Ile | Ser | Arg | Ser | Ser | Thr | Leu | Arg | Ser | Ala | Asn | Ser | Ala | Val | Ser | Val | |
| 575 | | | | | 580 | | | | | 585 | | | | | | |
| TGG | ACG | GAT | ATA | AGT | GAT | ATA | GTA | GAT | TCA | ACG | GAT | AAT | GTC | GTA | ACA | 1825 |
| Trp | Thr | Asp | Ile | Ser | Asp | Ile | Val | Asp | Ser | Thr | Asp | Asn | Val | Val | Thr | |
| 590 | | | | | 595 | | | | | 600 | | | | | 605 | |
| GCC | ACG | GCA | ACA | GCC | GCT | GCG | AAG | AAA | TTC | AGA | GTC | AAA | GAA | TTT | ACG | 1873 |
| Ala | Thr | Ala | Thr | Ala | Ala | Ala | Lys | Lys | Phe | Arg | Val | Lys | Glu | Phe | Thr | |
| | | | | 610 | | | | | 615 | | | | | 620 | | |
| ACA | GAG | TTT | AAT | GGC | GTT | AGT | TTT | GAT | GAC | ATA | TCT | GCT | GCT | GTT | GTA | 1921 |
| Thr | Glu | Phe | Asn | Gly | Val | Ser | Phe | Asp | Asp | Ile | Ser | Ala | Ala | Val | Val | |
| | | | 625 | | | | | 630 | | | | | 635 | | | |
| AAA | ACA | AAA | ATG | AAT | AAG | TTG | AAT | GTT | GTG | GAT | GAG | GAA | ATG | CTA | CCA | 1969 |
| Lys | Thr | Lys | Met | Asn | Lys | Leu | Asn | Val | Val | Asp | Glu | Glu | Met | Leu | Pro | |
| | | | 640 | | | | 645 | | | | | 650 | | | | |
| CAA | ATT | ATA | ACT | GAA | GCG | TCG | GAG | AAA | TTT | ATA | CCG | AAC | CGT | GCA | TAT | 2017 |
| Gln | Ile | Ile | Thr | Glu | Ala | Ser | Glu | Lys | Phe | Ile | Pro | Asn | Arg | Ala | Tyr | |
| 655 | | | | | 660 | | | | | 665 | | | | | | |
| AGA | TTA | ATA | GAT | GGA | GAT | AAA | GTA | TAC | GAG | GTT | ACA | ACG | GAA | GGG | AAG | 2065 |
| Arg | Leu | Ile | Asp | Gly | Asp | Lys | Val | Tyr | Glu | Val | Thr | Thr | Glu | Gly | Lys | |
| 670 | | | | 675 | | | | | 680 | | | | | 685 | | |
| TAT | TTT | GCT | TAT | TTG | ACA | GAA | ACA | TTC | GAA | GAG | GTA | ATG | TTC | GAT | GCA | 2113 |
| Tyr | Phe | Ala | Tyr | Leu | Thr | Glu | Thr | Phe | Glu | Glu | Val | Met | Phe | Asp | Ala | |
| | | | | 690 | | | | | 695 | | | | | 700 | | |
| GAG | AGA | TTT | GCT | GAG | TTA | GTT | ACT | TAT | TCG | CCC | GTA | ATA | TCA | GCA | ATT | 2161 |
| Glu | Arg | Phe | Ala | Glu | Leu | Val | Thr | Tyr | Ser | Pro | Val | Ile | Ser | Ala | Ile | |
| | | | 705 | | | | | 710 | | | | | 715 | | | |
| ATA | GAC | TTT | AAA | ACA | ATA | AAG | AAT | CTT | AAT | GAT | AAT | TAT | GGT | ATT | ACG | 2209 |
| Ile | Asp | Phe | Lys | Thr | Ile | Lys | Asn | Leu | Asn | Asp | Asn | Tyr | Gly | Ile | Thr | |
| | | 720 | | | | | 725 | | | | | 730 | | | | |
| AGG | GAA | CAA | GCA | TTA | AAC | ATG | TTA | CGT | TCA | GAT | CCG | AAA | GTA | TTG | AGA | 2257 |
| Arg | Glu | Gln | Ala | Leu | Asn | Met | Leu | Arg | Ser | Asp | Pro | Lys | Val | Leu | Arg | |
| 735 | | | | | 740 | | | | | 745 | | | | | | |
| AGC | TTT | ATT | AAT | CAA | AAC | AAT | CCT | ATA | ATT | AAA | AAC | AGA | ATA | GAG | CAA | 2305 |
| Ser | Phe | Ile | Asn | Gln | Asn | Asn | Pro | Ile | Ile | Lys | Asn | Arg | Ile | Glu | Gln | |
| 750 | | | | | 755 | | | | | 760 | | | | | 765 | |
| CTA | ATA | TTA | CAG | TGT | AGA | ATA | TAGAGCTGTG | AGGTGAGGAT | GTGACC | | | | | | | 2352 |
| Leu | Ile | Leu | Gln | Cys | Arg | Ile | | | | | | | | | | |
| | | | | 770 | | | | | | | | | | | | |

( 2 ) INFORMATION FOR SEQ ID NO:4:

( i ) SEQUENCE CHARACTERISTICS:
        ( A ) LENGTH: 772 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Arg  Ser  Leu  Ile  Tyr  Arg  Gln  Leu  Leu  Tyr  Asn  Ser  Tyr  Ser  Val
 1                   5                        10                       15

Asp  Leu  Ser  Asp  Glu  Ile  Thr  Asn  Ile  Gly  Ala  Glu  Lys  Lys  Glu  Asn
               20                        25                       30

Val  Thr  Val  Gln  Ile  Gly  Glu  Phe  Ala  Gln  Ser  Gln  Tyr  Ala  Pro  Val
          35                        40                       45

Ser  Trp  Gly  Ser  Gly  Glu  Thr  Leu  Ser  Gly  Asn  Val  Glu  Glu  Gln  Pro
     50                        55                       60

Leu  Asp  Gly  Pro  Tyr  Thr  Pro  Asp  Lys  Ser  Asn  Leu  Pro  Ser  Asn  Tyr
65                       70                       75                       80

Trp  Tyr  Leu  Ile  Asn  Pro  Ser  Asn  Asp  Gly  Val  Val  Phe  Ser  Val  Thr
                    85                        90                       95

Asp  Asn  Ser  Thr  Leu  Trp  Met  Phe  Thr  Tyr  Leu  Val  Leu  Pro  Asn  Thr
               100                       105                      110

Ala  Gln  Thr  Ser  Val  Val  Val  Asn  Val  Met  Asn  Glu  Thr  Val  Asn  Ile
          115                       120                      125

Ser  Ile  Asp  Asn  Ser  Gly  Ser  Ala  Tyr  Lys  Phe  Val  Asp  Tyr  Phe  Lys
     130                      135                      140

Thr  Ser  Ser  Ala  Gln  Ala  Tyr  Arg  Ser  Arg  Asn  Phe  Leu  Ile  Thr  Ala
145                      150                      155                      160

His  Arg  Leu  Gln  Ala  Tyr  Lys  Arg  Asp  Gly  Asp  Gly  Asn  Ile  Ser  Asn
                    165                      170                      175

Tyr  Trp  Gly  Ser  Asp  Ala  Tyr  Gly  Asp  Leu  Arg  Val  Gly  Thr  Tyr  Phe
               180                      185                      190

Asn  Pro  Val  Pro  Asn  Ala  Val  Ile  Asn  Leu  Asn  Ala  Asp  Phe  Tyr  Val
          195                      200                      205

Ile  Pro  Asp  Ser  Gln  Gln  Glu  Met  Cys  Thr  Glu  Tyr  Ile  Arg  Arg  Gly
     210                      215                      220

Leu  Pro  Ala  Ile  Gln  Thr  Thr  Thr  Tyr  Val  Thr  Pro  Ile  Ser  Tyr  Ala
225                      230                      235                      240

Val  Arg  Ser  Gln  Arg  Ile  Ala  Arg  Pro  Asn  Glu  Asp  Ile  Thr  Ile  Ser
                    245                      250                      255

Lys  Ala  Ser  Leu  Trp  Lys  Glu  Val  Gln  Tyr  Asn  Arg  Asp  Ile  Val  Ile
               260                      265                      270

Arg  Phe  Val  Phe  Ala  Asn  Asn  Ile  Ile  Lys  Ala  Gly  Gly  Leu  Gly  Tyr
          275                      280                      285

Lys  Trp  Ser  Glu  Ile  Ser  Tyr  Lys  Ala  Asn  Asn  Tyr  Gln  Tyr  Thr  Tyr
     290                      295                      300

Met  Arg  Asp  Gly  Ile  Glu  Val  Val  Ala  His  Thr  Thr  Val  Ser  Val  Asn
305                      310                      315                      320

Gly  Val  Ser  Val  Tyr  Asp  Tyr  Asn  Thr  Gly  Ser  Leu  Pro  Thr  Asp  Phe
                    325                      330                      335

Thr  Ile  Arg  Asn  Tyr  Asp  Val  Leu  Lys  Glu  Ser  Ser  Phe  Val  Tyr  Val
               340                      345                      350

Asp  Tyr  Trp  Asp  Asp  Ser  Gln  Ala  Phe  Arg  Asn  Met  Val  Tyr  Val  Arg
          355                      360                      365
```

```
Ser  Leu  Asn  Ala  Glu  Leu  Asn  Gln  Val  Gln  Cys  Val  Gly  Gly  His  Tyr
     370                 375                 380
Ser  Phe  Ala  Leu  Pro  Val  Gly  Ser  Trp  Pro  Val  Met  Gln  Gly  Gly  Ser
385                      390                 395                           400
Val  Val  Leu  Thr  Phe  Asp  Gly  Val  Thr  Leu  Ser  Thr  Gln  Phe  Thr  Asp
                   405                 410                      415
Tyr  Val  Ser  Leu  Asn  Ser  Leu  Arg  Phe  Arg  Phe  Arg  Cys  Ala  Val  Ser
               420                 425                      430
Glu  Pro  Pro  Phe  Arg  Val  Thr  Gly  Thr  Arg  Ile  Ser  Asn  Leu  Tyr  Gly
          435                      440                 445
Leu  Pro  Ala  Ala  Asn  Pro  Met  Gly  Asp  Gln  Gln  Tyr  Glu  Ala  Ser
     450                      455                 460
Gly  Arg  Phe  Ser  Leu  Ile  Ser  Leu  Val  Pro  Ser  Asn  Asp  Asp  Tyr  Gln
465                      470                      475                      480
Thr  Pro  Ile  Ala  Asn  Ser  Val  Thr  Val  Arg  Gln  Asp  Leu  Glu  Arg  Gln
               485                      490                      495
Leu  Asp  Glu  Met  Arg  Arg  Glu  Phe  Asn  Glu  Leu  Ser  Ala  Asn  Ile  Ala
               500                 505                      510
Leu  Ser  Gln  Leu  Ile  Asp  Leu  Ala  Leu  Leu  Pro  Leu  Asp  Met  Phe  Ser
          515                 520                 525
Met  Phe  Ser  Gly  Ile  Arg  Ser  Thr  Ile  Glu  Ala  Ala  Lys  Asn  Phe  Ala
     530                      535                      540
Thr  Ser  Val  Met  Lys  Lys  Phe  Arg  Lys  Ser  Asn  Leu  Ala  Lys  Ser  Val
545                      550                 555                           560
Asn  Ser  Leu  Thr  Asp  Ala  Ile  Thr  Asp  Ala  Ala  Gly  Ser  Ile  Ser  Arg
                   565                 570                      575
Ser  Ser  Thr  Leu  Arg  Ser  Ala  Asn  Ser  Ala  Val  Ser  Val  Trp  Thr  Asp
               580                 585                      590
Ile  Ser  Asp  Ile  Val  Asp  Ser  Thr  Asp  Asn  Val  Val  Thr  Ala  Thr  Ala
          595                 600                      605
Thr  Ala  Ala  Ala  Lys  Lys  Phe  Arg  Val  Lys  Glu  Phe  Thr  Thr  Glu  Phe
     610                 615                      620
Asn  Gly  Val  Ser  Phe  Asp  Asp  Ile  Ser  Ala  Ala  Val  Val  Lys  Thr  Lys
625                      630                 635                           640
Met  Asn  Lys  Leu  Asn  Val  Val  Asp  Glu  Glu  Met  Leu  Pro  Gln  Ile  Ile
               645                      650                      655
Thr  Glu  Ala  Ser  Glu  Lys  Phe  Ile  Pro  Asn  Arg  Ala  Tyr  Arg  Leu  Ile
               660                 665                      670
Asp  Gly  Asp  Lys  Val  Tyr  Glu  Val  Thr  Thr  Glu  Gly  Lys  Tyr  Phe  Ala
          675                 680                      685
Tyr  Leu  Thr  Glu  Thr  Phe  Glu  Glu  Val  Met  Phe  Asp  Ala  Glu  Arg  Phe
     690                 695                      700
Ala  Glu  Leu  Val  Thr  Tyr  Ser  Pro  Val  Ile  Ser  Ala  Ile  Ile  Asp  Phe
705                 710                      715                           720
Lys  Thr  Ile  Lys  Asn  Leu  Asn  Asp  Asn  Tyr  Gly  Ile  Thr  Arg  Glu  Gln
               725                 730                      735
Ala  Leu  Asn  Met  Leu  Arg  Ser  Asp  Pro  Lys  Val  Leu  Arg  Ser  Phe  Ile
               740                 745                      750
Asn  Gln  Asn  Asn  Pro  Ile  Ile  Lys  Asn  Arg  Ile  Glu  Gln  Leu  Ile  Leu
          755                      760                 765
Gln  Cys  Arg  Ile
770
```

ROTAVIRUS STRAIN G9P11

This application is a continuation of application Ser. No. 08/231,041 filed Apr. 15, 1994, now abandoned.

BACKGROUND OF THE INVENTION

Rotaviruses are members of the family Reoviridae and contain 11 segments of double-stranded RNA (dsRNA) enclosed within a double-protein shell virion. Each segment encodes a single viral polypeptide, for a total of five non-structural and six structural proteins (15). Three viral polypeptides, VP4, VP6, and VP7 induce antibodies used to serologically classify rotaviruses. The VP4 and VP7 outer-capsid proteins independently induce antibodies associated with type-specific neutralization and protection from infection (38,40,51,71,72). The dual serotype specificities defined by antibodies to the VP4 and VP7 proteins are designated P and G, respectively (15). Rotaviruses have also been classified by hybridization analysis into families of genes or genogroups, based on the number of gene segments that form stable hybrid bands between strains (16,64). At least three genogroups designated Wa, DS1 and AU1, have been recognized among human rotaviruses (64). Several genogroups have also been recognized in animal rotaviruses from cattle, pigs, and monkeys (63).

A neonatal rotavirus strain from Bangalore, India has recently been described (89). The rotaviruses of this strain are serotype G10P11, and by hybridization analysis their genome showed homology to genes from both a bovine serotype G10 strain and moderate identity to several genes of the human Wa genogroup (13). Two additional reports have characterized human rotavirus strains with one to multiple genes related to bovine isolates as indicated by hybridization analyses, sequence analysis, or both (1,66).

Rotaviruses are the single most important etiologic agents of severe diarrheal illness of infants and young children world-wide (Barnett, B. *Med. Clin. North America* 67:1031–1058, 1983), and cause 35–50% of hospitalization for this condition during the first 2 years of life. In developing countries, rotaviruses are usually the leading cause of life-threatening disease in infants and young children.

In developed countries, rotaviruses are the major etiological agents of diarrhea in infants and young children. This disease is not usually a life-threatening illness in developed countries, because of greater access to treatment and improved techniques for rehydrating patients who are infected with the virus. However, even in developed countries, rotavirus infection has a significant economic impact due to the loss of work hours by parents attending to sick children.

A Venezuelan rotavirus strain from newborns, M37, has been developed as a vaccine candidate, but was found to be less immunogenic than an alternative vaccine candidate, rhesus rotavirus (21), which also has low efficacy.

Thus, a need exists for a vaccine and immunization method against rotavirus infection, which is provided by the present invention.

SUMMARY OF THE INVENTION

The invention provides an isolated rotavirus of the strain G9P11, an isolated nucleic acid encoding the rotavirus of strain G9P11 and a purified antigen specific for the rotavirus. An isolated nucleic acid encoding the antigen of the rotavirus is also provided, as is an isolated nucleic acid that selectively hybridizes under high stringency conditions with the nucleic acid encoding the virus.

A purified antibody which selectively binds the virus of strain G9P11 is provided. The G9P11 rotavirus in a pharmaceutically acceptable carrier for administration in an immunization protocol is provided.

The invention provides an isolated rotavirus of strain G9P11, wherein the G9 gene is substituted. The invention further provides an isolated rotavirus of strain G9P11, wherein the P11 gene is substituted.

DETAILED DESCRIPTION OF THE INVENTION

Isolated Rotavirus

Figures 1A, 1B:
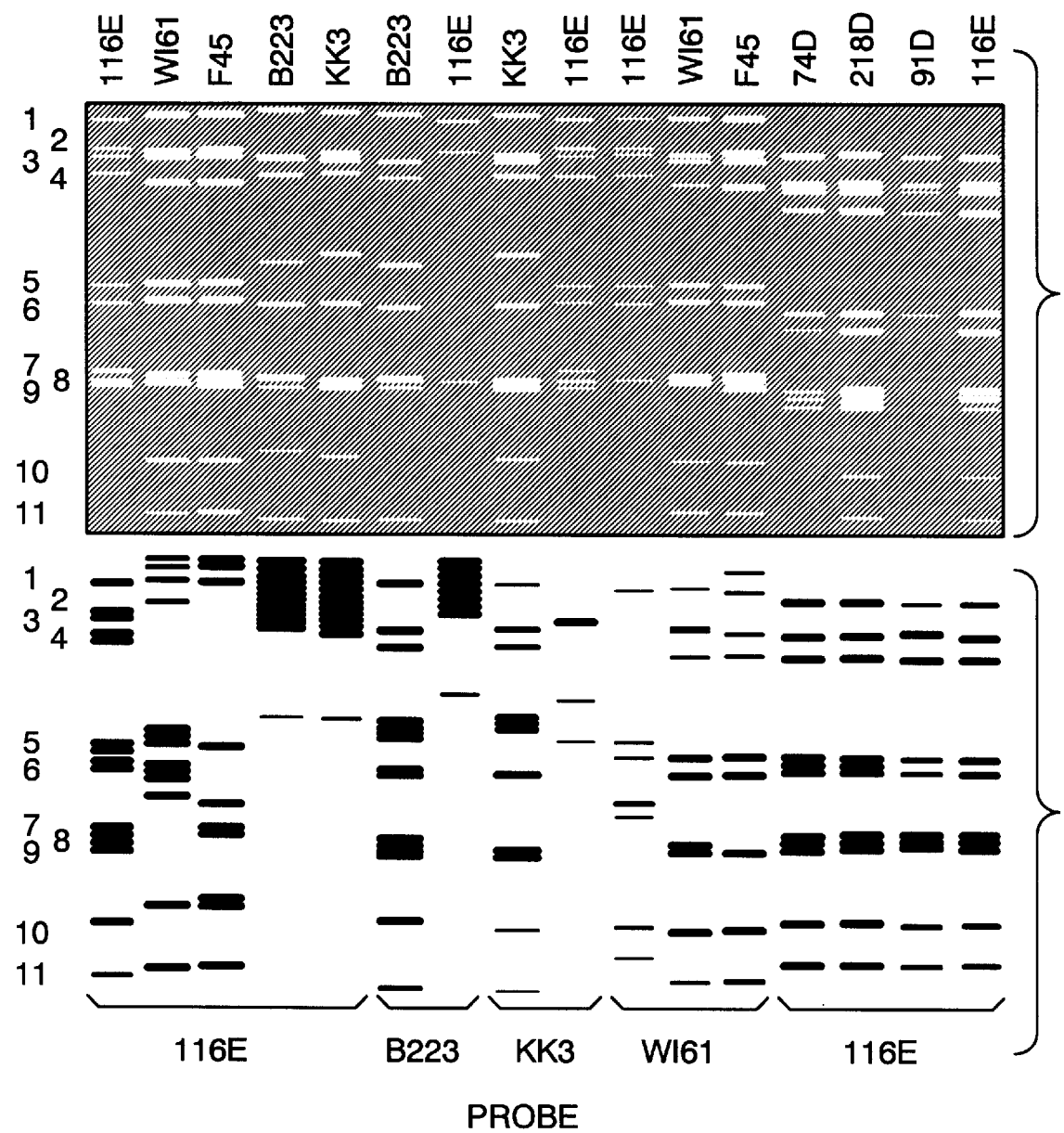
FIG. 1A is an ultraviolet light photograph of an electropherotype of RNA hybrids of the present rotavirus strain G9P11 and other strains.
FIG. 1B is an autoradiograph of an electropherotype of RNA hybrids of the present rotavirus strain G9P11 and other strains.

The invention provides an isolated rotavirus of a new rotavirus strain, designated herein as "strain G9P11." Rotaviruses of strain G9P11 have a genome comprising a bovine VP4 gene (Type P11) and a human VP7 gene (Type G9). "Isolated rotavirus" is defined as a viral preparation that is relatively free from other viral and cellular contaminants normally found in its natural environment, e.g., the gastrointestinal tract. This viral preparation is contemplated to be sufficiently separated from other viral and cellular contaminants to be acceptable for use in a therapeutic or research setting. For example, a virus preparation that has been sufficiently separated from other viral and cellular contaminants so that it is useful in a diagnostic assay, such as genogrouping, is "isolated." Specific examples of isolation procedures are provided in the Examples.

Whether a virus is of the strain G9P11 can be ascertained by number of methods which are known in the art. These include, but are not limited to polymerase chain reaction (RT-PCR), RNA hybridization, sequence analysis, and genogrouping (RNA electropherotyping).

Genogrouping:

Regarding the genogrouping method, a rotavirus of the strain G9P11 has a novel and distinct RNA/RNA hybrid electrophoresis pattern, compared to other rotavirus strains, which demonstrates it as a new strain. Briefly, genogrouping is accomplished by comparing the mobility of the eleven transcripts of the isolated rotaviruses with that of known strains. The genogrouping method involves 1) isolating double stranded viral RNA from various rotavirus samples (both unknown isolates and viruses of reference strains), 2) hybridizing the isolated RNAs with in vitro transcribed probe RNAs, 3) hybridizing the probes with the isolated RNAs for a standard period of time and under standard hybridization conditions, and 4) determining the relative mobility of the hybrids by nondenaturing polyacrylamide gel electrophoresis.

The relative mobility of the RNA hybrids indicates the genogroup to which each of the isolated RNA samples is a member. Quantitative differences in the positions of the hybrids on the gel indicate that the viruses are of different strains. In contrast, similar mobility patterns indicate that the viruses are of the same strain.

In an example from the art, Nakagomi et al. (65) employed genogrouping analysis to define a newly isolated human rotavirus, which was related to a distinct feline rotavirus strain. Thus, the genogrouping method provides a reliable method of distinguishing novel rotavirus strains from known strains and permits the accurate classification of new virus isolates within existing strains.

Genogrouping is used herein to identify several rotavirus isolates as a new genogroup (strain), designated G9P11, which is distinct from known rotavirus strains (Example 2 and FIG. 1). The virus isolates that fall within the present rotavirus strain G9P11 are characterized as having a bovine VP4 (Subtype P11) genome substitution for the human counterpart gene and a subtype G9 VP7 gene. The present invention, to date, is the first rotavirus having this genogroup and genotype. Previously unknown virus isolates named 116E, 74D, 218D, and 91D, isolated by the inventors are all shown by genogrouping to be members of the same new rotavirus strain G9P11 (Example 2 and FIG. 1). Other virus isolates can be classified as strain G9P11 or distinguished from the present strain using this method. However, it is noteworthy that other novel rotaviruses provided in the invention in addition to G9P11 are expected to have different genogrouping patterns as a result of having certain nonessential gene substitutions.

RT-PCR:

The present rotavirus strain G9P11 can be detected utilizing a nucleic acid amplification technique, such as reverse transcriptase polymerase chain reaction (RT-PCR). By detecting the presence of both the P11 and G9 sequences in a sample of RNA extracted from a rotavirus, it can be ascertained that the virus does not belong to any previously known strains.

For example, primers which hybridize only with nucleic acids specific for members of rotavirus strain G9P11 can be utilized. The presence of an amplification product indicates the presence of a virus of the strain. Generally, this reaction would comprise contacting RNA obtained from a sample of the unknown virus with a primer which selectively hybridizes to the VP4 gene (subtype P11) sequence and synthesizing the first strand RT-PCR product. A second primer, either within the VP4 gene, or located in an adjacent gene would serve as the primer for the second strand synthesis. Primers can have substitutions so long as enough complementary bases exist for selective hybridization (Kunkel et al. *Methods Enzymol.* 1987:154:367, 1987). The presence of the bovine VP4 (P11) gene is necessary for synthesis of the final RT-PCR product, and therefore for the positive result indicating the presence of a rotavirus in a sample that is of the strain G9P11. Examples of primers that amplify the P11 sequence are provided below in Example 3.

Because strain G9P11 has the G9 sequence of the VP7 gene, amplification of this gene in addition to P11 is further evidence that the unknown virus is of strain G9P11. A method for RT-PCR amplification of the G9 sequence including primers is provided in Example 2. By this or other RT-PCR methods using primers specific for G9 and for P11, rotavirus isolates can be identified as G9P11. This conclusion can be confirmed by genogrouping.

Purified Antigen

A purified antigen specific for a rotavirus of the invention is provided. The antigen can include purified antigenic peptides, polypeptide fragments or intact proteins encoded by the virus and nucleic acids of the present invention are also contemplated. As used herein, "purified" means the antigen is sufficiently free of contaminants or other viral components with which the antigen normally occurs to distinguish the antigen from the contaminants or components. The purified antigen and antigenic fragments of the present invention are also referred to herein as "the antigen."

An antigenic fragment of the antigen can be isolated from the whole antigen by chemical or mechanical disruption. The purified fragments thus obtained can be tested to determine their antigenicity and specificity by the well known methods noted herein. Antigenic fragments of the antigen can also be synthesized directly. An immunoreactive fragment is defined as an amino acid sequence of at least about 5 consecutive amino acids derived from the antigen amino acid sequence. The antigen of the present invention can also be a recombinant protein obtained by cloning nucleic acids encoding the protein in an expression system capable of producing the protein or fragments thereof as described below.

Once the amino acid sequence of the antigen is provided, it is also possible to synthesize, using standard peptide synthesis techniques, peptide fragments chosen to be homologous to immunogenic regions of the antigen and to modify these fragments by inclusion, deletion or modification of particular amino acids residues in the derived sequences. Thus, synthesis or purification of an extremely large number of peptides derived from the antigen is possible.

For example a novel VP4 antigen is provided (SEQ ID NO:2). Rotaviruses of strain G9P11 possess this surface protein, which differs from other VP4 antigens as further described below in Example 3.

Nucleic Acids

An isolated nucleic acid encoding the antigen specific for a rotavirus of the invention is also provided. An isolated nucleic acid encoding the novel rotavirus of the invention is also provided.

An isolated nucleic acid that selectively hybridizes under high stringency conditions with the nucleic acid of G9P11 and has at least 70% complementarity with the segment of the nucleic acid of G9P11 to which it hybridizes is also provided. As used herein to describe nucleic acids, the term "selectively hybridizes" excludes the occasional randomly hybridizing nucleic acids. The selectively hybridizing nucleic acids can be used, for example, as probes or primers for detecting the presence of a rotavirus that has the nucleic acid to which it hybridizes. Thus, the invention provides a method of detecting rotavirus G9P11 infection in a subject, comprising detecting the presence of the selectively hybridizing nucleic acid in a specimen from the subject, the presence of the nucleic acid indicating infection with rotavirus G9P11.

The selectively hybridizing nucleic acids of the invention can have at least 70%, 80%, 85%, 90%, 95%, 97%, 98% and 99% complementarity with the segment of the sequence to which it hybridizes. The nucleic acids can be at least 12, 50, 100, 150, 200, 300, 500, 750, 1000, 2000, 3000 or 4000 nucleotides in length. Thus, the nucleic acid can be a coding sequence for the rotavirus G9P11, or can be used as a probe or primer for detecting the presence of rotavirus G9P11. If used as primers, the invention provides compositions including at least two nucleic acids which selectively hybridize with different regions so as to amplify a desired region. Depending on the length of the probe or primer, it can range between 70% complementary bases and full complementarity and still hybridize under stringent conditions. For example, for the purpose of diagnosing the presence of rotaviurs G9P11, the degree of complementarity between the hybridizing nucleic acid (probe or primer) and the sequence to which it hybridizes (rotaviral RNA from a sample) should be at least enough to exclude hybridization with a nucleic acid from related virus. Thus, a nucleic acid that selectively hybridizes with a rotavirus G9P11 sequence will not selectively hybridize under stringent conditions with a nucleic acid of a segment of another strain, and vice versa. The invention provides examples of these nucleic acids of G9P11 rotavirus so that the degree of complementarity required to distinguish selectively hybridizing from nonselectively hybridizing nucleic acids under stringent conditions can be clearly determined for each nucleic acid. "High stringency conditions" refers to the hybridization conditions used in a hybridization protocol, for example, RNA/RNA hybridization, as in the genogrouping method. In general, these conditions should be a combination of temperature and salt concentration chosen so that the denaturation temperature is approximately 5°–20° C. below the calculated $T_m$, of the hybrid under study. The temperature and salt conditions are readily determined empirically in preliminary experiments in which samples of reference RNA are hybridized to the primer nucleic acid of interest and then amplified under conditions of different stringencies. The stringency conditions are readily tested and the parameters altered are readily apparent to one skilled in the art. For example, $MgCl_2$ concentrations used in the reaction buffer can be altered to increase the specificity with which the primer binds to the template, but the concentration range of this compound used in hybridization reactions is narrow, and therefore, the proper stringency level is easily determined.

Vaccines

One embodiment of the present invention provides a rotavirus which can be used to provide protection against rotaviral infection and subsequent episodes of diarrhea comprising administering to patients the rotavirus of strain G9P11 either alone or in pharmaceutically acceptable carrier.

Rotaviruses, which are responsible for diarrheal diseases, replicate in the gastrointestinal tract of humans. Mucosal immunity plays a significant role in resistance to reinfection by viruses that replicate exclusively in mucosal membranes. The present avirulent rotavirus strain G9P11, therefore, fills a well established need by stimulating mucosal immunity against infection by virulent strains of rotaviruses.

Active immunization can be achieved through natural infection with strain G9P11, or it can be acquired artificially through vaccination (Kuby, J. Immunology W. H. Freeman and Co. New York, 1992). Strain G9P11 is attenuated so that it has lost its pathogenicity but it has retained the capacity for growth within the host. Attenuated viruses such as the present invention have the advantage of being better able to confer immunity through a single immunization. This is particularly important in underdeveloped countries where patients are less likely to return for subsequent immunization boosters. The present rotavirus, however, has the additional ability to replicate within the patient, which makes is particularly suitable to induce cell-mediated immunity.

Immunogenic amounts of the virus can be determined using standard procedures. Briefly, various concentrations of the present attenuated virus or a putative immunogenic antigen are prepared, administered to patients, and the immunogenic response (e.g., the production of antibodies to the virus or cell mediated immunity) to each concentration is determined. Techniques for monitoring the immunogenic response of patients after infection with rotaviruses are very well known in the art. For example, samples can be assayed using enzyme linked immunosorbent assays (ELISA) to detect the presence of rotavirus antibodies, such as serum IgA (Hjelt, et al. J. Med. Virol. 21:39–47, 1987). The specificity of a putative immunogenic antigen of G9P11 can be ascertained by testing sera, other fluids or lymphocytes from the inoculated patient for cross-reactivity with other closely related rotaviruses.

The amounts of whole rotavirus or antigen administered depend on the subject, the condition of the subject, the size of the subject, etc. Thereafter, a patient so inoculated with the putative immunogen is usually naturally exposed to an unattenuated rotavirus, which permits one to make a determination of the potential vaccine effect of the specific immunogenic fragment. For example, amounts of rotavirus strain G9P11 expected to be immunogenic in an immunization protocol can range from $10_{-4}$ to $10_7$ pfu (21) Other rotavirus immunization protocols referenced in the art provide immunogen ammounts and standard techniques.

The pharmaceutically acceptable carrier or adjuvant in the vaccine of the present invention can be selected by standard criteria (Arnon, R. (Ed.) Synthetic Vaccines I:83–92, CRC Press, Inc. Boca Raton, Fla., 1987). By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. The carrier or adjuvant may depend on the method of administration and the particular patient.

Methods of administration can be by oral or sublingual means, or by injection. Actual methods of preparing the appropriate dosage forms are known, or will be apparent, to those skilled in this art; for example, see *Remington's Pharmaceutical Sciences* (Martin, E. W. (ed.) latest edition Mack Publishing Co., Easton, Pa.

Genetically Engineered Derivatives of G9P11

Given the present discovery of a novel replicating avirulent rotavirus, numerous modifications can be made to the virus using well known genetic engineering techniques. General protocols for generating a rotavirus reassortant are briefly as follows: 1) mixedly infect monolayers of MA104 cells with each of two rotavirus strains at 5 plaque forming units (PFU)/cell for each strain (for example, a virulent G2P4 strain from India plus G9P11); 2) incubate infected cells for 24–36 hrs at 37° C. and then harvest and freeze the monolayer at −70° C.; 3) freeze-thaw the cell-lysate 3 times, centrifuge to remove the cell debris and store the supernatant at −70° C.; 4 analyze the supernatant by plaque assay at appropriate dilutions in the presence of an appropriate dilution of neutralizing G9 serum (to suppress plaque formation by strains having the 116E VP7 gene); 5) pick plaques and prepare a cell lysate as described above and analyze the individual lysates by TR-PCR specific for G2 and P11 VP7 and VP4 genes, respectively; 6) analyze the G2P11 strains by genogrouping to determine if only the G2 VP7 gene is derived from the G2 parent (i.e., ideally the 10 genes should be from 116E; 7) prepare a seed stock of the reassortant.

Thus, the invention provides the rotavirus of strain G9P11, wherein the G9 (VP7) gene is substituted to generate a new virus. One of the unique characteristics of the present strain is that it possesses a subtype sequence for the P11 (VP4) gene, which is similar to the bovine subtype (strain B223) VP4 gene, against a background of human subtypes for the other rotavirus genes, including the VP7 gene. Thus, the VP7 gene can be substituted with other sequences to generate a new virus having the same P11 gene that is in the present rotavirus, but possessing a different VP7 gene. In this manner one of the uniqueness of the P11 sequence, against a human background, is maintained in the mutant. The substitutions can be of the sequences of other known VP7 genes from other rotavirus strains or the substitutions can comprise variations in the G9 sequence that are not otherwise known.

The invention also provides the rotavirus of strain G9P11, wherein the P11 (VP4) gene is substituted to generate a new virus. For example, a sequence that encodes a protein that is strongly immunogenic can be substituted for the P11 gene in order to enhance the efficacy of the rotavirus as a vaccine.

Additionally, because the presence of the G9 subtype and P11 subtype in a rotavirus is novel, substitutions within the other genes can be made without changing the unique character of the present rotavirus. For example, genes 1–3, 5, 6 and 8–11 of the present G9P11 viruses can be any of the subtypes for those genes and still fall within the scope of the present disclosure. They can be modifications of the known subtypes so long as the essential function, if any, of each gene is maintained. The rotaviruses so constructed will not exhibit the same RNA electropherotype pattern as the strain designated G9P11. However, they will share with G9P11 the unique feature of the P11 gene against a mostly human background.

By providing the nucleotide sequence for the nucleic acid encoding the antigen, the present invention also permits the making of specific point mutations having the desired effect.

In a further embodiment of the present invention a mutated rotavirus engineered as described herein can be used to provide protection against rotaviral infection and subsequent episodes of diarrhea comprising administering to patients the genetically engineered reassortant rotavirus either alone or in pharmaceutically acceptable carrier.

Vectors and Hosts

A vector comprising the nucleic acids of the present invention is also provided. The vectors of the invention can be in a host capable of expressing the antigen.

There are numerous *E. coli* expression vectors known to one of ordinary skill in the art useful for the expression of the antigen. Other microbial hosts suitable for use include bacilli, such as Bacillus subtilus, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroproration may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted DNAs in mammalian cells (such as COS7).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Purified Antibodies

A purified antibody which selectively binds the rotavirus of the invention is provided. The antibody can be a purified monoclonal antibody that specifically binds the rotavirus or antigen specific for the rotavirus. The antibodies can specifically bind a unique epitope of the antigen. "Specifically binds" as used herein describes an antibody or other ligand that does not cross react substantially with any antigen other than the one specified, in this case, the rotavirus antigen. Antibodies can be made as described in the art (see also, Harlow and Lane, *Antibodies; A Laboratory manual*, Cold Spring Harbor Laboratory, Cold Spring Harbor, N.Y. 1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen DNA clone libraries for cells secreting the antigen. Those positive clones can then be sequenced as described in the Examples or by other methods (see, for example, Kelly et al., *Bio/Technology* 10:163–167, 1992 and Bebbington et al., *Bio/Technology* 10:169–175, 1992).

The antibody can be bound to a substrate or labeled with a detectable moiety or both bound and labeled. The detectable moieties contemplated with the composition of the present invention are those listed below in the description of the diagnostic methods, including fluorescent, enzymatic and radioactive markers.

Immunological Diagnosis of Rotavirus Infection

A method of diagnosing rotavirus strain G9P11 infection in a subject comprises a) contacting an antibody-containing sample from the subject with an amount of a virus of the rotavirus strain G9P11 sufficient to permit a detectable antibody-antigen binding reaction; and b) detecting the presence of the binding reaction, the presence of the binding reaction indicating rotavirus strain G9P11 infection.

In the diagnostic methods taught herein, the rotavirus or specific antigen can be immobilized on a substrate and contacted by a fluid sample such as serum, urine, saliva or other fluid. This sample can be taken directly from the patient or in a partially purified form. In this manner, antibodies specific for the rotavirus (the primary antibody) will specifically bind the immobilized antigen. Thereafter, a secondary antibody bound to, or labeled with, a detectable moiety (radioactive label or dye) can be added to enhance the detection of the primary antibody. Thus, for example, several molecules of the secondary antibody can react with each primary antibody, making the primary antibody more detectable.

The present invention provides a method of specifically detecting the presence of the G9P11 rotavirus possessing a bovine-derived VP4 gene (G11) as described above. The present invention provides reagents which can be used to detect the presence of the new virus sample, comprising detecting the presence of nucleic acids encoding the virus.

The following examples are intended to illustrate, but not limit, the invention. While the protocols described are typical of those that might be used, other procedures known to those skilled in the art may be alternatively employed.

EXAMPLES

Example 1

Protection Conferred by Neonatal Rotavirus Strain G9P11 Infection Against Subsequent Rotavirus Diarrhea A cohort of newborns in New Delhi who were nosocomially infected with rotavirus during their first days of life were monitored to determine whether neonatal infection protected these children against subsequent episodes of rotavirus diarrhea. Rotavirus infection occurred in 60% of newborns by the fourth day of life, was asymptomatic, and was associated with a single strain having a single electropherotype (strain G9P11). Field workers visited children between the ages of 3 months and 2 years twice weekly to identify diarrheal episodes during follow up and to test fecal specimens from these episodes for rotavirus by enzyme immunoassay. The 148 children with neonatal strain G9P11 infection had 46% fewer attacks of rotavirus diarrhea during the follow up period than the 56 infants without nosocomial infection (0.23 vs 0.42 episodes per child/per year, $P<0.05$). Protection conferred by neonatal infection was concentrated among infants in their first year of life and was not associated with a significant decrease in the severity of disease. The asymptomatic nature of neonatal rotavirus infection and the significant protection it confers against subsequent rotavirus diarrhea indicate that immunization of Indian newborns with this strain provides an approach to the prevention of rotavirus diarrhea.

Study Participants.

The study was conducted in New Delhi between November, 1986 and October, 1988. Fecal specimens from babies born in the maternity unit at AIIMS were screened for rotavirus infection prior to discharge from the hospital. Infants were eligible for the study if they were healthy with no major congenital anomaly, had a gestational age of 37 weeks or more, weighed more than 2500 grams at birth, and lived within a 7-km radius of AIIMS. The study was explained to the mothers, whose verbal consent was required for recruitment.

A total of 238 infants were screened during the enrollment period and 34 were excluded because they were not successfully monitored beyond 3 months-of-age. Of the 204 infants who remained, 148 (73%) were neonatally infected and 56 (27%) were not. Follow up was very complete: the total days for which data were available (64,058 for neonatally infected, 25,410 for uninfected) included 99% of the total expected by adding all days from the time of birth to the last home visit minus acceptable days of absence (e.g., vacation days away from home).

The two groups were compared to identify factors that might distinguish the groups or affect the incidence of diarrhea during follow up (Table 1). The neonatally infected group did not differ significantly from the uninfected in their gestational ages, birth weights, gender distribution, duration of hospital stay, prevalence of diarrhea in the hospital, likelihood to be breast-fed, mother's education, or duration of follow up.

Definition of Neonatal Exposure.

Fecal specimens from newborns were screened for rotavirus infection daily during their hospital stay. After discharge, the infants were visited daily for 4 days by trained field workers who collected fecal specimens, which were used to identify rotavirus infection that might have been missed in the hospital or prolonged shedding of the strain. Children were defined as neonatally infected if rotavirus was detected in their fecal specimens during either the hospitalization or the 4 days after discharge. The remaining infants in whom no rotavirus was detected were considered to be unexposed (controls).

Surveillance for Rotavirus Diarrhea.

The period of follow up ranged from 23 months for infants recruited at the beginning of the study to 14 months for those infants recruited at the end. Field workers visited each child twice a week, queried mothers about symptoms of diarrhea in their child since the last visit, and collected a stool specimen if diarrhea had occurred since the last visit.

Follow up for diarrhea began when an infant reached 3 months of age. For these children, diarrhea was defined as the passage of 3 or more liquid or semi-liquid stools or a single watery stool per day. The duration of diarrhea was coded as the period from the day of onset to the day preceding recovery. Diarrheal illness separated by 48 hours of normal stools were considered to be distinct episodes. Rotavirus diarrhea was defined to be an episode of diarrhea in which viral antigen was detected in the stool specimen. No attempt was made to characterize the rotaviruses detected during follow up to determine, for instance, if protection was better for homotypic vs. heterotypic strains.

For every diarrheal episode, the field workers completed a standardized questionnaire about associated symptoms (i.e., the presence of fever, vomiting, dehydration, days and severity of diarrhea, and treatment by a physician or in a hospital). The status of dehydration of a child was assessed by the field workers on the basis of criteria noted in the World Health Organization (WHO) guidelines (99). The field workers routinely provided oral rehydration solution or referred children to health workers in the outpatient service for other treatment or medication.

Children were removed from the cohort if they were unavailable for follow up for a continuous 6-week period or if they moved beyond the 7-km radius of AIIMS. For periods in which the child was unavailable for one or more home visits, recall was limited to a maximum of 10 days before the next home visit.

Antigen Detection.

Stool specimens were tested for rotavirus antigen by using an enzyme-linked immunosorbent assay (ELISA) prepared and distributed by WHO. All specimens found to be positive were confirmed by using a blocking assay. Selected strains from newborns were examined by polyacrylamide electrophoresis (PAGE) with silver staining (37,54) to assess whether the newborn infections were caused by a single strain. PAGE was carried out as described using 7.5%, 14 cm gels run at 100 volts for 6 h at room temperature.

Duration of Rotavirus Shedding.

Rotavirus strain G9P11 shedding among neonates was monitored during the hospital stay and the 4 days following discharge. The pattern of infection was consistent with nosocomial infection. Neonatal infection was first detected during the second day of life, and the likelihood of infection increased daily thereafter, affecting 50% by day 3–4 and 85% by 1 week.

Many newborns shed rotavirus for a prolonged period of time (Table 2). When the frequency of rotavirus excretion was tabulated by duration of hospital stay, a number of newborns were found to shed rotavirus for periods of more than one week and one child shed rotavirus for all 13 days of his hospital stay.

The electropherotypes of 100 neonatal isolates were examined to assess whether they were of a single type consistent with nosocomial spread or distinct indicating multiple sources of infection. An electrophoretic type was identified for 71 isolates and the pattern seen persisted in strains detected throughout the study period.

Estimation of Protective Efficacy.

The incidence of all diarrhea and rotavirus diarrhea was calculated for both the neonatally infected and non-infected groups (Table 3), which were monitored for 140 and 55 child-years, respectively. A total of 396 episodes of diarrhea occurred during follow up of which 55 were associated with rotavirus. The neonatally infected group had 22% fewer episodes of diarrhea and 46% fewer episodes of rotavirus diarrhea during the follow up period. The decreased incidence of rotavirus diarrhea occurred among infants in the first year of life. By the second year of life, rotavirus diarrhea was uncommon in both the neonatally infected and control groups, and the difference in incidence between groups was not significant.

The severity of episodes of rotavirus diarrhea was compared between infants who were neonatally infected and those who were not (Table 4). Rotavirus diarrhea in the neonatally infected group tended to be less severe and was associated with less fever, vomiting, dehydration and a shorter duration of illness, but none of these symptoms was significantly different between groups.

Statistical Analysis.

Statistical analyses were performed by Epi-info (version 5), using Mantel-Haenzel chi-square or Fisher's exact 2-tailed test. Statistical significance was defined as P<0.05.

The days of follow up were tallied and used to calculate child-years at risk and incidence of diarrhea in the analysis of protection (i.e., efficacy). The efficacy of neonatal rotavirus infection to protect against subsequent rotavirus diarrhea was calculated as the incidence of rotavirus diarrhea in the neonatally uninfected group versus that in the infected group, divided by the incidence in the uninfected group (multiplied by 100).

Two children had two episodes of rotavirus diarrhea in the follow up period. Because the results of protection were comparable whether or not multiple episodes were included or excluded, all data were included.

TABLE 1

Comparison of newborns with and without neonatal rotavirus infection

| Characteristic | Infected (N = 148) | Not Infected (N = 56) |
|---|---|---|
| Gestational Age (wks)* | 38.6 ± 1.5 | 38.9 ± 2.1 |
| Birthweight (grams) | 2981 ± 445 | 3023 ± 359 |
| Gender (% female) | 53 | 54 |
| Hospital stay - days | 3.8 (1–12) | 3.7 (1–12) |
| Diarrhea in hospital (episodes/100 children) | 7 | 9 |
| Breast-fed % | 47 | 48 |
| Duration of breast-feeding‡ (weeks ± SD) | 66.8 ± 41.2 | 64.3 ± 46.8 |
| Education of mother-yrs | 11.0 (0–19) | 10.6 (0–21) |
| Mean days of follow up | 433 | 454 |

None of the differences between groups are significant.
*Values given as means ±SD, or mean and (range) except when otherwise noted.
‡Values for exclusive breast-feeding in weeks (63.3 ± 37.1 vs. 60.0 ± 37.4).

TABLE 2

Frequency of rotavirus excretion in stools among neonates related to duration of hospital stay

| Days in which rotavirus excreted | _____ Days of hospitalization _____ | | | | | | | | | |
|---|---|---|---|---|---|---|---|---|---|---|
| | 5 | 6 | 7 | 8 | 9 | 10 | 11 | 12 | 13 | $\leq 14$ |
| 1 | — | 5 | 2 | 2 | — | 1 | 3 | — | 1 | — |
| 2 | 4 | 8 | 4 | 2 | 2 | 1 | 2 | 1 | — | 1 |
| 3 | 6 | 26 | 18 | 3 | 2 | 1 | 4 | 3 | — | 1 |
| 4 | 4 | 34 | 19 | 9 | 6 | 4 | 5 | 2 | 1 | 2 |
| 5 | 4 | 38 | 19 | 12 | 7 | 4 | 5 | 4 | — | 2 |
| 6 | — | 35 | 19 | 14 | 3 | 6 | 5 | 4 | 1 | 3 |
| 7 | | | 16 | 11 | 4 | 3 | 7 | 1 | 1 | 3 |
| 8 | | | | 11 | 3 | 5 | 6 | 3 | 2 | 3 |
| 9 | | | | | 2 | 2 | 4 | 5 | 2 | 3 |
| 10 | | | | | | 3 | 4 | 1 | 2 | 2 |
| 11 | | | | | | | 3 | 3 | — | 1 |
| 12 | | | | | | | | 4 | 2 | 1 |
| 13 | | | | | | | | | 1 | 1 |
| 14 | | | | | | | | | | 2 |
| Mean + SD | 2.25 ± 1.3 | 3 ± 1.1 | 2.9 ± 1.6 | 3.4 ± 1.7 | 3.6 ± 1.2 | 3.3 ± 2.9 | 6 ± 3.4 | 3.9 ± 1.9 | 6.5 ± 0.7 | 7.5 ± 3.5 |
| Range | 1, 4 | 1, 5 | 1, 7 | 1, 7 | 2, 5 | 1, 9 | 1, 11 | 1, 7 | 7, 13 | 5, 10 |

TABLE 3

Protection conferred by neonatal rotavirus infection against subsequent diarrhea

| Outcome | Neonatally Infected Incidence* (n) | Non-Infected Incidence (n) | % Efficacy (95% C.I.) |
|---|---|---|---|
| All diarrhea | | | |
| Episodes | 1.89 (264) | 2.42 (132) | 22 (4–37) |
| Days | 16 (2237) | 19.4 (1059) | 17 (11–23) |
| Rotavirus diarrhea | | | |
| Episodes | .23 (32) | .42 (23) | 46 (7–68) |
| Days | 2.1 (300) | 3.6 (196) | 40 (36–48) |
| Rotavirus diarrhea by age | | | |
| 3–5 months | .29 (10) | .61 (8) | 52 (−21 to 81) |
| 6–11 months | .29 (18) | .62 (8) | 53 (5–76) |
| 12 months | .09 (4) | .05 (1) | −71 (−143 to 81) |

Incidence = events/child-year
n = number of events used in the calculation of incidence

TABLE 4

Symptoms of rotavirus diarrhea during follow up in children who were neonatally infected with rotavirus versus those who were not

| | % (n) with symptoms | |
|---|---|---|
| Symptoms | Neonatally Infected (N = 32) | Not Infected (N = 24) |
| Fever* | 13(4) | 33(8) |
| Vomiting | 22(7) | 29(7) |
| Dehydration | 3(1) | 8(2) |
| Diarrhea Severity (motions/day) | | |
| 7 | 28(9) | 33(8) |
| 8–15 | 56(18) | 58(14) |
| 16 | 16(5) | 8(2) |
| Duration | | |
| 1–5 days | 40(13) | 29(7) |
| 5 days | 60(19) | 71(17) |

*Difference between groups, P = 0.06 by chi-squared test. Fever defined as an axillary temperature $\geq 99.5°$ F.

Example 2

Characterization of the G Serotype and Genogroup of New Delhi Newborn Rotavirus Isolate 116E Viruses.

Rotavirus strains were grown in MA104 cells and purified by density gradient centrifugation (23,59). The culture-adapted standard strains used previously for neutralization tests were also used in this study including: Wa, DS1, P, ST3, OSU, UK, CH2, 69M, WI61, B223, YM, L26, L338, and F123 (serotypes $G_1$ to $G_{14}$) (100). Strains KK3 (serotype $G_{10}P_7$) and F45 (serotype $G_9P_8$) were used for RNA-RNA hybridization studies (31,92). Strain WI61×UK is a single segment reassortant containing the VP7 gene from WI61 (serotype $G_9$) and 10 genes from rotavirus UK (serotype $G_6P_5$). Culture-adapted neonatal strains 116E, 91D, 218D and 74D were originally collected at the All India Institute of Medical Sciences (AIIMS) Hospital between 1987 to 1988 and were isolated after two passages in primary AGMK cells and eight passages in MA104 cells (24). Isolate 116E was subsequently plaque-purified twice in MA104 cells before use in these experiments (84). Eighteen culture-adapted strains subgrouped with the monoclonal antibodies of Greenberg, including those used in this study, were found to be subgroup II (33) (not shown).

Rotavirus-positive, neonatal fecal specimens 4D (Kasturba Hospital), and 56E, 88E, and 90D (AIIMS Hospital) were collected in 1991–1992 in New Delhi, India.

Hyperimmune Sera.

Sera to standard rotavirus strains and isolate 116E were prepared in guinea pigs free of rotavirus-specific neutralizing antibodies, using partially purified virus as the inoculum (100). Sera were heat inactivated by treatment at 56° C. for 30 min before PRN assays (100).

PRN

These tests were performed with MA104 cells in 6-well plates (Costar, Cambridge, Mass.) (100). Serial fourfold dilutions of each sera (from 1:80 to 1:81,920) were mixed with trypsin-treated virus suspensions and diluted to give 50 PFU per well. The end-point titer was expressed as the reciprocal of the last serum dilution that gave a 60% or more reduction in the number of plaques compared with the control. Strains were assigned to the same G type if the difference in titer between homologous and heterologous neutralizing antibodies was 20-fold or greater.

Oligonucleotide Primers.

Primers were synthesized in the Molecular Biology Core Facility of the Centers for Disease Control and Prevention.

RT-PCR.

The consensus primer con 3, and the type-specific primers 1T-1, 2T-1, 3T-1, 4T-1, and 5T-1 were used to identify rotavirus strains with P types 8, 4, 6, 9 and 10, respectively (23). The classification system used for P types in this study was described by Estes and Cohen (15). To detect strains with a VP4 gene related to 116E, a primer complementary to nucleotides 116 to 133 of gene 4 of this strain was designed and used it in a mixture with primers con 3, and 1T-1, 2T-1, 3T-1, 4T-1, and 5T-1 (24). A one-amplification RT-PCR typing procedure was used throughout this study. RNA was extracted from 10% fecal suspensions with glass powder and subjected to one cycle of reverse-transcription (60 min at 42° C.), 30 cycles of PCR (1 min at 94° C., 2 min at 42° C., and 3 min at 72° C.) and a final extension cycle (7 min at 72° C.) and then analyzed on agarose gels (23).

Nucleotide Sequencing.

The VP7 gene of isolate 116E was sequenced with complementary primers, using the dideoxy chain-termination method and viral transcript RNA prepared in vitro (18,81). Regions of secondary structure and other ambiguities were sequenced from dsRNA and PCR DNA, using plus-sense primers (24,27).

Nucleotide Sequence Accession Number.

The VP7 gene of isolate 116E has been assigned a nucleotide sequence accession number of L14072.

Sequence Analysis of Isolate 116E VP7 gene.

Data analysis for this gene was performed using the Genetics Computer Group (GCG), University of Wisconsin package of programs (12). The following GenBank accession numbers were used for VP7 gene sequences: Wa (serotype $G_1$), K02033; S2 (serotype $G_2$), M11164; RRV (serotype $G_3$), M21650; ST3 (serotype $G_4$), X13603; OSU (serotype $G_5$), X06722; NCDV (serotype $G_6$), M12394; TY1 (serotype $G_7$), L01098; B37 (serotype $G_8$), J04334; B223 (serotype $G_{10}$), X52650; YM (serotype $G_{11}$), M23194; L26 (serotype $G_{12}$), M58290; L338 (serotype $G_{13}$), D00843; F123 (serotype $G_{14}$), M61876; I321 (serotype $G_{10}$), L07658; and I321 VP4 (serotype $P_{11}$), M92986. For strain WI61, the published sequence was used for analysis (31).

To determine the genetic relationship of isolate 116E with other rotavirus G serotypes, its VP7 gene was sequenced (SEQ ID NO:1). This gene is 1061 nucleotides long, one nucleotide shorter than that of most rotavirus VP7 genes, but identical in length to those of serotype $G_9$ strains F45 and WI61 (31). Alignment of the VP7 gene sequences of 116E with other rotaviruses suggests that a deletion within a TAG termination codon (thus converting the sequence of the termination codon from TAG to TGA) could account for the size difference between this strain and most other rotaviruses (not shown). A similar explanation was proposed to account for the length of the F45 and WI61 VP7 genes (31). Like many rotavirus VP7 genes, the 116E VP7 gene encodes two long open reading frames (ORFs), beginning with in-phase methionine initiation codons at nucleotides 49 to 51 and 136 to 138, and ending with a single termination codon at nucleotides 1027 to 1029. The calculated molecular mass of the protein encoded by the longer ORF (326 amino acids) is 37,162 daltons.

To determine relationships to other rotaviruses the nucleotide and deduced amino acid sequences of the 116E VP7 gene were compared with those of representative members of G serotypes 1 to 14 (Table 5). The highest homologies were with the serotype $G_9$ strain WI61, suggesting that isolate 116E was a member of this G serotype. An alignment of the amino acid sequences of the VP7 protein of 116E with those of $G_9$ strains WI61 and F45 and, for comparison, with $G_3$ isolates RRV and P supports this hypothesis. In total, 26 (strains F45 and WI61) or 46 to 53 (isolates RRV and P) amino acid differences are present in the VP7s of these rotaviruses compared with the 116E VP7. In the regions of VP7 proteins that are normally highly divergent between members of different G serotypes (amino acids 87–100, 142–150. and 208–221), only six substitutions were found between 116E and F45 or WI61 VP7s, compared with 14 and 15 substitutions for strains RRV and P, respectively (14,26,31). It was noted, however that the amino acid sequence of the 116E VP7 protein is substantially more divergent from the VP7s of strains WI61 or F45 (26 amino acid differences) than the VP7s of these two strains are from each other (5 amino acid differences) (31).

The VP7 of isolate 116E shared several features with other rotaviruses including the conserved glutamine at residue 51 that becomes the amino terminal end of the mature protein after removal of the signal sequence, and the presence of a conserved N-glycosylation site at residues 69–71. A second potential N-glycosylation site at residues 145–147 is found only on the VP7 protein of some human or bovine $G_{10}$ strains (eg, B223 and A64) although some isolates have one at residues 146–148 (1,15,92). Unlike the VP7 of strain F45, and like the VP7 of strain WI61, the VP7 of isolate 116E does not have a glycosylation site at residue 20–22 (31).

Cross-neutralization between isolate 116E and other rotaviruses.

Sequence analysis of the VP7 gene of isolate 116E suggested a strong antigenic relatedness to serotype $G_9$, and less relatedness to other G serotypes. To determine the true antigenic relationships, cross-neutralization tests were carried out, using hyperimmune guinea pig sera to the 14 known G serotypes and with sera to isolate 116E (Table 6). As shown here, strong two-way cross-neutralization between strains 116E and the serotype $G_9$ isolate WI61 was found, demonstrating that isolate 116E belongs to serotype $G_9$ based on a 20-fold or greater difference between homologous and heterologous neutralizing antibody titers in the PRN test. This conclusion is supported by the finding of strong cross-neutralization between 116E and the serotype $G_9$ single-segment reassortant WI61×UK, which contains only the VP7 gene of strain WI61 and the remaining 10 genes from the serotype $G_6$ isolate UK. In addition, weak two-way cross-neutralization between strains 116E and B223 (end point titers=1:80) was found, presumably due to the antigenic relationship between their VP4 proteins (24, 35). Strain WI61×UK sera also neutralized the $G_6$ rotavirus UK, which is probably mediated by neutralizing antibodies to the VP4 proteins of UK and WI61×UK. No cross-neutralization was observed using sera to the other 12 G serotypes.

Genogrouping of Neonatal Rotaviruses.

Probes for hybridization were synthesized from purified single-shelled virus particles by in vitro transcription in the presence of [$^{32}$P]-GTP (64). For hybridization, dsRNA samples were heat denatured (100° C., 2 min), mixed with 10,000 cpm of labeled probe, and then hybridized for 16 h at 65° C. in a standard buffer (100 mM NaCl, 1 mM EDTA, 0.1% sodium dodecyl sulfate (SDS), 50 mM Tris-HCl, pH 8.0) (FIG. 1A). The hybridized samples were then resolved by discontinuous polyacrylamide gel electrophoresis (PAGE) on a 10% gel (64). Gels were stained with ethidium bromide to visualize dsRNA bands before autoradiography (FIG. 1B).

The results of sequencing and serologic studies suggested that isolate 116E was a reassortant between strains related to bovine $P_{11}$ and human $G_9$ rotaviruses (24. Table 6). Therefore, to analyze the genetic relationship between other genes of 116E and prototype strains with serotype $G_9$ or $P_{11}$, specificity, genogroup analysis was performed (64). When a probe to isolate 116E was hybridized to dsRNA from isolate 116E, eleven hybrid bands comigrated with the corresponding homologous dsRNA segments (FIG. 1). Strong hybridization (seven or eight hybrid bands formed) was also obtained between the 116E probe and RNAs from strains WI61 and F45, although many of these hybrids migrated at a slightly different speed than the homologous products (FIG. 1). A similar pattern was obtained between this probe and strain Wa (not shown). In contrast, when probe 116E was hybridized to denatured bovine B223 or KK3 RNA, one strong band migrating between segments three and four, and one weak band migrating between segments 4 and 5 were observed. Hybridization to strain DS1 RNA was minimal (DS1 genogroup, not shown).

To confirm these results, probes from B223 (bovine genogroup), KK3 (bovine genogroup), and WI61 (Wa genogroup) were hybridized to homologous RNAs and to 116E RNA (FIG. 1B., probes B223, KK3, and WI61). As expected, eleven hybrid bands (which comigrated with the corresponding homologous dsRNA segments) were formed between the three probes and corresponding minus strands. The WI61 probe also formed at least ten hybrids with strain F45, most of which comigrated with homologous hybrids. The bovine probes formed one strong (migrating between segments one and two) and one weak (migrating between segments four and five) hybrid band with isolate 116E RNA, in agreement with the results of the reciprocal experiment. The WI61 probe formed eight bands of moderate-to-weak intensity, with slightly anomalous migration patterns, when hybridized to 116E RNA, the homology between the genes of isolate 116E and other rotavirus isolates from this collection were also analyzed, using a 116E probe. The results (FIG. 1B, last four lanes) demonstrated that all four isolates analyzed are one strain, as suggested by their identical electropherotypes.

This example describes the G serotype and genogroup of isolate 116E and other rotaviruses of strain G9P11, a group of novel neonatal rotaviruses from New Delhi, India. Several of the New Delhi rotaviruses (116E, 74D, 91D, 218D) were studied by hybridization analysis with a isolate 116E probe, and, as expected from their identical electropherotypes, all segments hybridized with high homology, demonstrating that they belong to the same genogroup (strain).

TABLE 5

Homology between the VP7 gene of isolate 116E and those of other rotaviruses

| | | % sequence identity with other rotaviruses | |
|---|---|---|---|
| strain[a] | G serotype | nt[b] | aa[c] |
| Wa | 1 | 76.3 | 78.5 |
| S2 | 2 | 74.6 | 74.8 |
| RRV | 3 | 79.6 | 85.9 |
| ST3 | 4 | 76.0 | 76.4 |
| OSU | 5 | 78.2 | 80.4 |
| NCDV | 6 | 75.9 | 81.6 |
| TY1 | 7 | 66.2 | 61.1 |
| B37 | 8 | 74.9 | 79.1 |
| WI61 | 9 | 89.6 | 92.0 |
| B223 | 10 | 76.5 | 80.7 |
| YM | 11 | 78.8 | 83.1 |
| L26 | 12 | 76.9 | 80.4 |
| L338 | 13 | 75.5 | 76.1 |
| F123 | 14 | 78.7 | 81.9 |

[a]The following rotavirus VP7 gene sequences were used to prepare this table: Wa (Richardson et al., 1984), S2 (Both, unpublished data), RRV (Mackow et al., 1988), ST3 (Reddy et al., 1989), OSU (Rushlow et al., 1988), NCDV (Glass et al., 1985), TY1 (Kookl and Holmes, unpublished data), B37 (Hum et al., 1989), WI61 (Green et al., 1989), B223 (Xu et al., 1991), YM (Ruiz et al., 1988), L26 (Taniguchi et al., 1990), L338 (Browning et al., 1991a), F123 (Browning et al., 1991b).
[b]nucleotide
[c]amino acid

TABLE 6

Antigenic relationships between isolate 116E and other group A rotaviruses

| | | Reciprocal of the 60% PRN antibody titer with Guinea Pig hyperimmune antisera to the indicated virus strain | | | | | | | |
|---|---|---|---|---|---|---|---|---|---|
| strain (G type) | | Wa | DST | P | ST3 | OSU | UK | CH2 | 69M |
| Wa | (1) | 10240 | — | — | — | — | — | — | — |
| DS-1 | (2) | —[a] | 2560 | — | — | — | — | — | — |
| P | (3) | — | — | 10240 | — | — | — | — | — |
| ST3 | (4) | — | — | — | 20480 | — | — | — | — |
| OSU | (5) | — | — | — | — | 20480 | — | — | — |
| UK | (6) | — | — | — | — | — | 10240 | — | — |
| CH2 | (7) | — | — | — | — | — | — | 10240 | — |
| 69M | (8) | — | — | — | — | — | — | — | 10240 |
| WI61 | (9) | — | — | — | — | — | — | — | — |
| B223 | (10) | — | — | — | — | — | — | — | — |

TABLE 6-continued

Antigenic relationships between isolate 116E and other group A rotaviruses

| | | | | | | | | | |
|---|---|---|---|---|---|---|---|---|---|
| YM | (11) | — | — | — | — | — | — | — | — |
| L26 | (12) | — | — | — | — | — | — | — | — |
| L338 | (13) | — | — | — | — | — | — | — | — |
| F123 | (14) | — | — | — | — | — | — | — | — |
| WI61 × UK | (9) | — | — | — | — | — | — | — | — |
| 116E | | <80 | <80 | <80 | <80 | <80 | <80 | <80 | <80 |

Reciprocal of the 60% PRN antibody titer with Guinea Pig hyperimmune antisera to the indicated virus strain

| strain (G type) | | WI61 | 8223 | YM | L26 | L338 | F123 | WI61 × UK | 116E |
|---|---|---|---|---|---|---|---|---|---|
| Wa | (1) | — | — | — | — | — | — | — | <80 |
| DS-1 | (2) | — | — | — | — | — | — | — | <80 |
| P | (3) | — | — | — | — | — | — | — | <80 |
| ST3 | (4) | — | — | — | — | — | — | — | <80 |
| OSU | (5) | — | — | — | — | — | — | — | <80 |
| UK | (6) | — | — | — | — | — | — | 2560 | <80 |
| CH2 | (7) | — | — | — | — | — | — | — | <80 |
| 69M | (8) | — | — | — | — | — | — | — | <80 |
| WI61 | (9) | 20480 | — | — | — | — | — | 10240 | 10240 |
| B223 | (10) | — | 10240 | — | — | — | — | <80 | 80 |
| YM | (11) | — | — | 40960 | — | — | — | — | <80 |
| L26 | (12) | — | — | — | 20480 | — | — | — | <80 |
| L338 | (13) | — | — | — | — | 20480 | — | — | <80 |
| F123 | (14) | — | — | — | — | — | 40960 | — | <80 |
| WI61 × UK | (9) | — | — | — | — | — | — | 20480 | 10240 |
| 116E | | 10240 | 80 | <80 | <80 | <80 | <80 | 10240 | 10240 |

[a]not done

Example 3

Similarity of the VP4 Protein of Human Rotavirus Isolate 116E to that of the Bovine B223 Strain Rotavirus isolate 116E was isolated from the fecal specimen of a newborn infant from New Delhi who had no symptoms of diarrhea. The 4th gene segment that encodes the VP4 protein using viral transcript RNA prepared in vitro was sequenced. This gene is 2,353 base pairs in length and codes for a protein 772 amino acids long which begins with a methionine initiation codon at nucleotides 11 to 13 and ends with a single termination codon at nucleotides 2327 to 2329. Northern blot analysis demonstrates that the VP4 protein of this strain is encoded by genome segment 4. This gene is closely related to the VP4 gene of the bovine B223 P type 11 strain at both the nucleotide (90.8% identity) and amino acid (92.2% identity) levels, but is unique from those of strains from types 1 to 10. The close relatedness of the VP4 proteins of strains 116E and B223 is demonstrated by the amino acid composition of the potential trypsin cleavage sites and their flanking sequences, the size of the cleavage fragments, and conservation of most cysteine and proline residues. Comparative amino acid analysis of the variable regions thought to be important in VP4 antigenicity are consistent with the hypothesis that isolate 116E represents the first reported human P type 11 strain.

Culture of Rotavirus.

Isolate 116E was isolated from a newborn infant who excreted rotavirus but had no symptoms. The strain was culture-adapted by two passages in primary African Green Monkey Kidney cells and four passages in MA104 cells. This strain was then plaque-purified twice (94) and grown in quantity in MA104 cells. Virus was purified by Genetron extraction and $CsCl_2$ equilibrium density gradient centrifugation and viral transcript RNA was prepared as described by Flores (22). Sequencing of transcript RNA was carried out by the Sanger dideoxy-chain termination method (22) using a commercially available RNA sequencing kit (Boehringer-Mannheim, Indianapolis, Ind.) and [$^{35}$S] deoxyadenosine 5'-[α-thio]triphosphate (NEN Research Products, Boston, Mass.) as the radioactive precursor as described previously (81).

Sequencing of the VP4 Gene.

To sequence the 5' terminal one third of this gene, the consensus oligonucleotide con 2. which is complementary to nucleotides 887 to 868 in strain KU segment 4 (47) was used to prime the first sequencing reaction (10) presented at the American Society for Virology meeting, Ithaca, N.Y., 1991). The first complementary primer near the 3' terminus was identified by sequencing purified, polyadenylated (95) segment 4 transcript RNA using an oligo dT primer with two G residues at its 3'end (83). Additional primers were then selected every 200–250 bases thereafter to complete the sequence (27). Primers were synthesized in the Biotechnology Core Facility of the Centers for Disease Control. The last 50 nucleotides at the 3' end were sequenced using dsRNA as a template and primers corresponding to regions 129 to 112 and 65 to 48 nucleotides from the terminus (27).

Regions of secondary structure and other ambiguities in this gene were solved using plus-sense primers and genomic dsRNA or RT-PCR products as the templates (27). PCR DNA was purified on spin-columns (Pharmacia-LKB, Piscataway, N.J.) according to the manufacturers instructions and sequenced using the Sequenase version 2.0 kit (USB, Cleveland, Ohio), according to the kit protocol with the exceptions that the DNA was denatured by boiling at 100° C. for 3 min, and then snap-cooled in dry ice-ethanol before addition of the reaction components. Using RNA sequencing, the first two nucleotides at the 5' end and the last residues at the 3' terminus could not be read. To confirm that these residues were conserved, double stranded cDNA from isolate 116E genomic RNA was synthesized by ligation of an 18 base oligonucleotide (primer 1) onto the 3' ends of the plus and minus strands followed by reverse-transcription of the ligation product using a second oligonucleotide (primer 2) complementary to the first (58). Double stranded DNAs containing the terminal regions plus an additional 18 bases corresponding to primer 1 and its complement were then synthesized from the cDNA, or the RNA ligation-product, by PCR amplification using oligonucleotide primer 2 and specific primers complementary to nucleotides 133 to 116 from the 5' terminus, or corresponding to nucleotides 2,003 to 2,020 from the 3' end of the VP4 gene. These DNAs were then purified on spun-columns and sequenced to confirm the identity of the terminal nucleotides.

The nucleotide sequence of gene 4 of isolate 116E (SEQ ID NO:3) was compared with that of strain B223. This gene is 2,353 nucleotides in length which makes it 6 and 9 residues shorter than the corresponding genes of most human and animal isolates and 1 nucleotide longer than the gene 4 of strain B223 (35). It contains one long open reading frame (ORF) beginning with a methionine initiation codon at nucleotides 11 to 13 and ending with a single termination codon at nucleotides 2327 to 2329 (SEQ ID NO:3). The predicted protein is 772 amino acids in length with a molecular mass of 86,882 daltons. This gene is unique among group A rotavirus VP4 genes in that the methionine initiation codon begins at nucleotide 11, rather than 10. This is due to the insertion of a T residue between nucleotides 4 to 6 compared to the VP4 genes of strain B223 (55) and other rotaviruses (SEQ ID NO:3). The P11 sequence of the 116E isolate of the present strain has been deposited with the GenBank/EMBL Data Libraries.

The nucleotide and deduced amino acid sequences of isolate 116E VP4 gene were compared with those from strains with P type 1 to 11 specificity (Table 7). P types were defined originally by comparative sequencing and hybridization studies showing that the VP4 proteins of rotavirus strains fell into several groups based on high (92 to 99%) and low (72% to 78% amino acid identity) within and between groups, respectively (27). Subsequent cross-neutralization studies showed that closely related strains (92 to 99% amino acid identity) were antigenically indistinguishable and were classified into P serotypes on this basis (35). The isolate 116E VP4 gene is closely related to that of the strain B223 at both the nucleotide (90.8% identical) and deduced amino acid (92.2% identical) levels but is unique from those of P type 1 to 10 strains (55.5 to 62.0% amino acid identity). The VP4 gene of B223 is different from all other strains studied to date based on both comparative amino acid analysis and cross-neutralization tests (28,55), and has been designated P serotype 11.

Amino Acid Sequence Comparison.

To determine if the VP4 protein of strain G9P11 (SEQ ID NO:3) shared other features with strain B223 the alignment of their deduced amino acid sequences was compared. The sequence alignment was prepared by sequentially using the University of Wisconsin, Genetics Computer Group (GCG) sequence analysis software programs (43) Lineup, Pileup and Pretty, using the algorithm of Needleman and Wunsch (44). Both proteins are 772 amino acids in length and have trypsin cleavage fragments that are 1 or 2 and 5 residues longer (VP8) and shorter (VP5), respectively, than the corresponding fragments of other VP4 proteins (27,29,47, 48,49,62,69,73,83,85). The trypsin cleavage site at amino acids 242 to 248 is completely conserved between the two strains, and only a single conservative amino acid substitution is found in the non-variable regions (AA 224 to 235 and 257 to 271) flanking this site. Four of the 5 cysteines and 27 of the 31 prolines in the VP4 protein of B223 are found in that of isolate 116E, suggesting a substantial structural conservation between the bovine strain and strain G9P11. Of the 60 amino acid substitutions between the VP4s of 116E and B223, 24 occur in hypervariable region of amino acids 71 to 204 and 580 to 608 that are thought to be important in P type determination (27,70). The overall amino acid identities (85.1%) in these regions between strains the present strain and B223 are somewhat lower than those of other strains within the same P type. Amino acids shown to be important for heterotypic neutralization by VP4-specific monoclonal antibodies (83,90) are completely conserved between isolate 116E and B223.

Northern Blot Analysis.

To determine the coding assignment of the isolate 116E VP4 protein, a Northern blot hybridization analysis was performed using a $^{32}$P-labelled RT-PCR product spanning the region between nucleotides 213 and 1252 as the probe. dsRNAs of isolate 116E and rotaviruses of P types 4, 6, and 8 to 10 were analysed. Rotavirus dsRNAs were electrophoresed for 1.5 hrs at 10 volts/cm on a 1.2% agarose gel, stained for 5 min with ethidium bromide, photographed under U.V. light, denatured for 20 min in 0.1M NaOH, and then transferred to a Nytran membrane (Schleicher and Scheull, Keene, NH) (45) and hybridized to a $^{32}$P-labelled dsDNA probe at 42° C. as described previously (46) using stringency conditions of 4×SSC, and 50% formamide. The nick-translated probe was prepared from a PCR product spanning nucleotides 214 to 1252 on isolate 116E gene 4.

The probe bound to isolate 116E segment 4 present in total genomic dsRNA (lane 6) or that purified from an acrylamide gel slice (lane 7), but not to the 4th segment of any of the control dsRNAs from P types 4, 6, and 8 to 10. This result demonstrates that the VP4 protein of G9P11 is encoded by segment 4.

These data demonstrate that the VP4 gene of strain G9P11 is unique from those of all human rotavirus strains analyzed to date but is closely related to that of the bovine P type 11 strain B223.

TABLE 7

Homology between the Gene 4 of Strain 116E and those of other rotaviruses

| | | % sequence identity with other rotaviruses | |
|---|---|---|---|
| strain[a] | G serotype | nt[b] | aa[c] |
| C486 | 1 | 59.7 | 59.8 |
| SA11 | 2 | 62.0 | 60.3 |
| RRV | 3 | 59.9 | 59.9 |
| RV-5 | 4 | 60.0 | 58.9 |
| UK | 5 | 60.2 | 59.6 |
| Gottfried | 6 | 60.7 | 57.5 |
| OSU | 7 | 60.8 | 59.8 |
| KU | 8 | 60.1 | 58.9 |
| K8 | 9 | 60.6 | 55.5 |
| 69M | 10 | 61.5 | 60.4 |
| B223 | 11 | 90.8 | 92.2 |

[a]The following rotavirus VP4 sequences were used to prepare this table: C486 (73), SA11 (62), RRV (58), RV-5 (48), UK, (49) Gottfried (29), OSU, (70), KU, (95), K8, (90) 69M, (74), and B223 (25).
[b]Nomemclature of Estes and Cohen (15)
[c]Nucleotide identity
[d]Amino acid identity

References

Throughout this application various publications are referenced by numbers within parentheses. Full citations for these publications may be found at the end of the specification immediately preceding the claims. The disclosures of these publications in their entireties are hereby incorporated by reference into this application in order to more fully describe the state of the art to which this invention pertains.

1. BEARDS, G., XU, L., BALLARD, A., DESSELBERGER, U., and MCCRAE, M. A. A serotype 10 human rotavirus. *J. Clin. Microbiol.* 30, 1432–1435, 1992.(10 X3)
2. BHAN, M. K., LEW, J. F., SAZAWAL, S., DAS, B. K., GENTSCH, J. R., and GLASS, R. I. (1993). Protection conferred by neonatal rotavirus infection against subsequent diarrhea. *J. Infect. Dis.* in press.
3. Bhan MK, Raj P, Bhandari N, et al. Role of enteric adenoviruses and rotaviruses in mild and severe acute enteritis. *Pediatric Infectious Diseases Journal* 7:320–3, 1988.(14 X1)
4. Bishop RF, Barnes GL, Cipriani E, Lund JS. Clinical immunity after neonatal rotavirus infection: A prospective longitudinal study in young children. *N Engl J Med* 309:72–6, 1983.(5 X1, also X2)
5. BROWNING, G. F., CHALMERS, R. M., FITZGERALD, T. A., and SNODGRASS, D. R. Serological and genomic characterisation of L338, a novel equine group A rotavirus G serotype. *J. Gen. Virol.* 72, 1059–1064, 1991a. (11 X3)
6. BROWNING, G. F., FITZGERALD, T. A., CHALMERS, R. M., and SNODGRASS, D. R. A novel group A rotavirus G serotype:serological and genomic characterization of equine isolate F123. *J. Clin. Microbiol.* 29, 2043–2046, 1991b. (7 X3)
7. BRYDEN, A. S., THOULESS, M. E., HALL, C. J., FLEWETT, T. H., WHARTON, B. A., MATHEW, P. M., and CRAIG, I. (1982). Rotavirus infections in a special-care baby unit. *J Infect* 4, 43–48.
8. CLARK, H. F., HOSHINO, Y., BELL, L. M., GROFF, J., HESS, G., BACHMAN, P., and OFFIT, P. A. (1987). Rotavirus isolate W161 representing a presumptive new human serotype. *J. Clin. Microbiol.* 25, 1757–1762.
9. Cook SM, Glass RI, LeBaron CW, Ho M-S. Global seasonality of rotavirus infections. *Bull WHO* 68:171–7, 1990.(18 X1)
10. DAS, M., DUNN, S. J., WOODE, G. N., GREENBERG, H. B., and RAO, C. D. (1993). Both surface proteins (VP4 and VP7) of an asymptomatic neonatal rotavirus strain (I321) have high levels of sequence identity with the homologous proteins of a serotype 10 bovine rotavirus. *Virology* 194, 374–379.
11. De Zoysa I, Feachem RG. Interventions for the control of diarrhoeal diseases among young children: rotavirus and cholera immunization. *Bull WHO* 63:569–83, 1985. (2. X1)
12. DEVEREUX, J., HAEBERLI, P., and SMITHIES, O. A comprehensive set of sequence analysis programs for the VAX. *Nuc. Acids Res.* 12, 387–395, 1984.(45 X3)
13. DUNN, S. J., GREENBERG, H. B., WARD, R. L., NAKAGOMI, O., BURNS, J. W., VO, P. T., PAX, K. A., DAS, M., GOWDA, K., and RAO, C. D. (1993). Serotype and genotypic characterization of human serotype 10 rotavirus for asymptomatic neonates. *J. Clin. Microbiol.* 31, 165–169.
14. DYALL-SMITH, M. L., LAZDINS, I., TREGEAR, G. W., and HOLMES, I. H. (1986). Location of the major antigenic sites involved in rotavirus serotype-specific neutralization. *Proc. Natl. Acad. Sci. USA* 83, 3465–3468.
15. ESTES, M. K., and COHEN, J. (1989). Rotavirus gene structure and function. *Microbiol. Rev.* 53, 410–449.(5 X3)
16. FLORES, J., PEREZ-SCHAEL, I., BOEGGEMAN, E., WHITE, L., PEREZ, M., PURCELL, R., HOSHINO, Y., MIDTHUN, K., CHANOCK, R. M., and KAPIKIAN, A. Z. (1985). Genetic relatedness among human rotaviruses. *J. Med. Virol.* 17, 135–143.
17. FLORES, J., HOSHINO, Y., BOEGGEMAN, E., PURCELL, R., CHANOCK, R. M., and KAPIKIAN, A. Z. (1986a). Genetic relatedness among animal rotaviruses. *Arch. Virol.* 87, 273–285.
18. Flores J, Midthun K, Hoshino Y, et al. Conservation of the fourth gene among rotaviruses recovered from asymptomatic newborn infants and its possible role in attenuation. *J Virol* 60(3):972–979, 1986.(6 X1, 1986b X2, 13 X3)
19. FLORES, J., PEREZ-SCHAEL, I., and KAPIKIAN, A. Z. (1989) Approaches to rotavirus vaccination in Viruses and the Gut. (M. J. G. FARTHING, Ed.), pp. 109–122. Smith, Kline and French: Welwin Garden City, UK.
20. Flores J, Kapikian AZ. Vaccines against viral diarrhoea. In: Tindall B, ed. *Balliere's Clinical Gastroenterology* 4:675–93, 1990.(8, X1)
21. Flores J, Perez-Schael I, Blanco M, et al. Comparison of reactogenicity and antigenicity of M37 rotavirus vaccine and rhesus-rotavirus-based quadrivalent vaccine. *Lancet* 2:330–4, 1990.(23 X1)
22. Flores, J., Myslinski, J., Kalica, A. R., Greenberg, H. B., Wyatt, R. G., Kapikian, A. Z., and Chanock, R. M., *J. Virol.* 43, 1032–1037 (1982). (26 X3)
23. Gentsch JR, Glass RI, Woods P, et al. Identification of group A rotavirus gene 4 types by polymerase chain reaction. *J Clin Microbiol* 30:1365–73, 1992.(25 X1, also X2, 22 X3)
24. GENTSCH, J., DAS, B. K., JIANG, B., BHAN, M. K., and GLASS, R. I. (1993). Similarity of the VP4 protein of human rotavirus strain 116E to that of the bovine B223 strain. *Virology* 194, 424–430.
25. Gerna, G., Sarasini, A., Parea, M., Arista, S., Miranda, P., Brussow, H., Hoshino, Y., and Flores, J., *J. Clin. Microbiol.* 30, 9–16 (1992). (9 X3)
26. GLASS, R. I., KEITH, J., NAKAGOMI, O., NAKAGOMI, T., ASKAA, J., KAPIKIAN, A. Z., CHANOCK, R. M., and FLORES, J. (1985). Nucleotide sequence of the structural glycoprotein VP7 gene of Nebraska calf diarrhea virus rotavirus: comparison with homologous genes from four strains of human and animal rotaviruses. *Virology* 141, 292–298.
27. Gorziglia M, Green K, Nishikawa K, et al. Sequence of the fourth gene of human rotaviruses recovered from asymptomatic or symptomatic infections. *J Virol* 62:2978–84, 1988.(24 X1, X2, 14 X3)
28. GORZIGLIA, M., LARRALDE, G., KAPIKIAN, A. Z., and CHANOCK, R. M. Antigenic relationships among human rotaviruses as determined by outer capsid protein VP4. *Proc. Natl. Acad. Sci. USA* 87, 7155–7159, 1990.(34 X3)
29. Gorziglia, M., Nishikawa, K., Hoshino, Y., and Taniguchi, K., *J. Virol.* 64, 414–418 (1990b). (37 X3)
30. GOUVEA, V., GLASS, R. I., WOODS, P., TANIGUICHI, K., CLARK, H. F., FORRESTER, B., and FANG, Z. Y. Polymerase chain reaction amplification and typing of rotavirus nucleic acids from stool specimens. *J. Clin. Microbiol.* 28, 276–282, 1990.(23 X3)
31. GREEN, K. Y., HOSHINO, Y., and IKEGAMI, N. (1989). Sequence analysis of the gene encoding the serotype-specific glycoprotein (VP7) of two new human rotavirus serotypes. *Virology* 168, 429–433.
32. Green KY, Taniguchi K, Mackow ER, Kapikian AZ. Homotypic and heterotypic epitope-specific antibody responses in adult and infant rotavirus vacinees: Implications for vaccine development. *J Infect Dis* 161:667–79, 1989.(22 X1)

33. GREENBERG, H., MCAULIFFE, V., VALDESUSO, J., WYATT, R., FLORES, J., KALICA, A., HOSHINO, Y., and SINGH, N. (1983). Serological analysis of the subgroup protein of rotavirus using monoclonal antibodies. *Infect. Immun.* 39, 91–99.
34. Greenberg, H. B., Flores, J., Kalica, A. R., Wyatt, R. G., and Jones, R., *J. Gen. Virol.* 64, 313–320 (1983a). Haffejee IE. Neonatal Rotavirus infections. *Rev Infect Dis* 13:957–62, 1991.(7 X1, 2 X3)
35. HARDY, M. E., GORZIGLIA, M., and WOODE, G. N. Amino acid sequence analysis of bovine rotavirus B223 reveals a unique outer capsid protein VP4 and confirms a third bovine VP4 type. *Virology* 191, 291–300, 1992.(33 X3)
36. HARDY, M. E., GORZIGLIA, M., and WOODE, G. N. (1993). The outer capsid protein VP4 of equine rotavirus strain H-2 represents a unique VP4 type by amino acid sequence analysis. *Virology* 193, 492–497.
37. Herring AJ, Inglis NF, Ojeh CK, Snodgrass DR, Menzies JD. Rapid diagnosis of rotavirus infection by direct detection of viral nucleic acid in silver-stained polyacrylamide gels. *J Clin Microbiol* 16:473, 1982.(17 X1)
38. HOSHINO, Y., SERENO, M. M., MIDTHUN, K., FLORES, J., KAPIKIAN, A. Z., and CHANOCK, R. M. Independent segregation of two antigenic specificities (VP3 and VP7) involved in neutralization of rotavirus infectivity. *Proc. Natl. Acad. Sci.* USA 82, 8701–8704, 1985a. (3 X3)
39. HOSHINO, Y., WYATT, R. G., FLORES, J., MIDTHUN, K., and KAPIKIAN, A. Z. (1985b). Serotypic characterization of rotaviruses derived from asymptomatic human neonatal infections. *J. Clin. Microbiol.* 21, 425–430.
40. HOSHINO, Y., SAIF, L. J., SERENO, M. M., CHANOCK, R. M., and KAPIKIAN, A. Z. (1988). Infection immunity of piglets to either VP3 or VP7 outer capsid protein confers resistence to challenge with a virulent rotavirus bearing the corresponding antigen. *J. Virol.* 62, 744–748.(4 X3)
41. HUM, C. P., DYALL-SMITH, M. L., and HOLMES, I. H. (1989). The VP7 gene of a new G serotype of human rotavirus (B37) is similar to G3 proteins in the antigenic C region. *Virology* 170, 55–61.
42. Institute of Medicine. The prospects of immunizing against rotavirus. In: New Vaccine Development: Volume 2. Diseases of importance in developing countries. Washington, D.C.: National Academy Press, D-13- to D-13-2, 1986.(3, X1, X2, 1 X3)
43. Isegawa, Y., Nakagomi, O., Nakagomi, T., and Ueda, S., *J. Gen. Virol.* 73, 1939–1946 (1992). (19 X3)
44. Jayashree S, Bhan MK, Raj P, et al. Neonatal rotavirus infection and its relation to cord blood antibodies. *Scan J Infect Dis* 20(3):249–53, 1988.(9 X1, 20 X3)
45. Jayashree S, Bhan MK, Kumar R, Bhandari N, Sazawal S. Protection against neonatal rotavirus infection by breast milk antibodies and trypsin inhibitors. *J Med Virol* 26:333–8, 1988.(10 X1)
46. Jayashree S, Bhan MK, Kumar R, Raj P, Glass R, Bhandari N. Serum and salivary antibodies as indicators of rotavirus infection in neonates. *J Infect Dis* 158:1117–20, 1988.(11 X1, 21 X3)
47. Jiang, B.-M., Tsunemitsu, H., Gentsch, J. R., Glass, R. I., Green, K. Y., Qian, Y., and Saif, L. J., *Virology* 190, 542–547 (1992). (28 X3)
48. Kantharidis, P., Dyall-Smith, M. L., and Holmes, I. H., Arch. Virol. 93, 111–121 (1987). (36 X3)
49. Kantharidis, P., Dyall-Smith, M. L., Tregear, G. W., and Holmes, I. H., *Virology* 166, 308–315 (1988). (38 X3)
50. Kapikian AZ, Flores J, Hoshino Y, et al. Rationale for the development of a rotavirus vaccine for infants and young children. *Progress in Vaccinology* 2:151–180, 1989.(1, x1)
51. KAPIKIAN, A. Z., and CHANOCK, R. M. O) Retro viruses. In *"Virology"* (B. N. FIELDS, D. M. KNIPE, R. M. CHANOCK, M. S. HIRSCH, J. L. MELNICK, T. P. MONATH, and B. ROIZMAN, Eds.), second ed., 2:1353–1404.Raven Press: New York, 1990.
52. Kapikian AZ, Chanock RM. Rotaviruses. In: *Virology.* (Ed: Fields, B.N.). second ed. v. 2:671–696.: Raven Press, 1990.(4 X1)
53. Kapikian, A. Z. and Chanock, R. M., In *"Virology"* (Fields, B. N., Ed.),pp. 863–906.Raven Press, New York, 1985.(6 X3)
54. Laemmli UK. Cleavage of structural proteins during the assembly of the head of bacteriophage T4. *Nature* 227:680–5, 1970.(16 X1)
55. Lambden, P. R., Cooke, S. J., Caul, E. O., and Clarke, I. N., *J. Virol.* 66, 1817–1822, 1992.(32 X3)
56. Larralde, G., Li, B., Kapikian, A. Z., and Gorziglia, M., *J. Virol.* 65, 3213–3218 (1991). (43 X3)
57. Larralde, G. and Flores, J., *Virology* 179, 469–473 (1990). (48 X3)
58. MACKOW, E. R., SHAW, R. D., MATSUI, S. M., VO, P. T., BENFIELD, D. A., and GREENBERG, H. B. Characterization of homotypic and heterotypic VP7 neutralization sites of Rhesus rotavirus. *Virology* 165, 511–517, 1988.(31 X3)
59. MASON, B. B., GRAHAM, D. Y., and ESTES, M. K. (1980). In vitro transcription and translation of simian rotavirus SA11 gene products. *J. Virol.* 33, 1111–1112.
60. MATSUDA, Y., ISEGAWA, Y., WOODE, G. N., ZHENG, S., KAGA, E., NAKAGOMI, T., UEDA, S., and NAKAGOMI, O. (1993). Two-way cross-neutralization mediated by a shared P (VP4) serotype between bovine rotavirus strains with distinct G (VP7) serotypes. *J. Clin. Microbiol.* 31, 354–358.
61. Matsuno, S., Hasegawa, A., Mukoyama, A., and Inouye, S., *J. Virol.* 54, 623–624 (1985). (8 X3)
62. Mitchell, D. B. and Both, G. W., *Nuc. Acids Res.* 17, 2122 (1989). (39 X3)
63. NAKAGOMI, O., and NAKAGOMI, T. (1991). Genetic diversity and similarity among mammalian rotaviruses in relation to interspecies transmission of rotavirus. *Arch. Virol.* 120, 43–55.
64. NAKAGOMI, O., NAKAGOMI, T., AKATANI, K., and IKEGAMI, N. (1989). Identification of rotavirus genogroups by RNA-RNA hybridization. *Mol. Cell. Probes* 3, 251–261.
65. Nakagomi O, Ohshima A, Aboudy Y, et al. Molecular identification by RNA-RNA hybridization of a human rotavirus that is closely related to rotaviruses of feline and canine origin. *J Clin Microbiol* 28:1198–203, 1990.(20 X1, also X2)
66. NAKAGOMI, O., KAGA, E., GERNA, G., SARASINI, A., and NAKAGOMI, T. (1992). Subgroup I serotype 3 human rotavirus strains with long RNA pattern as a result of naturally occurring reassortment between members of the bovine and AU-1 genogroups. *Arch. Virol.* 126, 337–342.
67. NAKAGOMI, T., OHSHIMA, A., AKATANI, K., IKEGAMI, N., KATSUSHIMA, N., and NAKAGOMI, 0.(1990). Isolation and molecular characterization of a serotype 9 human rotavirus strain. *Microbiol. Immunol.* 34, 77–82.
68. NEEDLEMAN, S. B., and WUNSCH, C. D. A general method applicable to the search for similarities in the amino acid sequence of two proteins. *J. Mol. Biol.* 48, 443–453, 1970. (46 X3)
69. Nishikawa, K., Taniguchi, K., Torres, A., Hoshino, Y., Green, K., Kapikian, A. Z., Chanock, R. M., and Gorziglia, M., *J. Virol.* 62, 4022–4026 (1988). (40 X3)
70. Nishikawa, K. and Gorziglia, M., *Nuc. Acids Res.* 16, 118–147 (1988). (42 X3)
71. OFFIT, P. A., and BLAVAT, G. (1986). Identification of two rotavirus genes determining neutralization specificities. *J. Virol.* 57, 376–378.
72. OFFIT, P. A., CLARK, H. F., BLAVAT, G., and GREENBERG, H. B. (1986). Reassortant rotaviruses containing structural proteins VP3 and VP7 from different parents induce antibodies protective against each parental serotype. *J. Virol.* 60, 491–496.
73. Potter, A. A., Cox, G., Parker, M., and Babiuk, L. A., *Nuc. Acids Res.* 15, 4361 (1987). (41 X3)
74. QIAN, Y., and GREEN, K. Y. Human rotavirus strain 69M has a unique VP4 as determined by amino acid sequence analysis. *Virology* 182, 407–412, 1991. (16 X3)
75. Raj P, Jayashree S, Bhan MK, Khoshoo V, Arora NK. RNA electropherotypes of rotaviruses excreted by asymptomatic neonates. *Indian J of Virol* 3(1–2):Jan. 12, 1987. (13 X1)
76. REDDY, D. A., GREENBERG, H. B., and BELLAMY, A. R. (1989). Nucleotide sequence of St. Thomas 3 rotavirus genomic segment 9: an RNA encoding the major serotypic antigen. *Nuc. Acids Res.* 17, 449.
77. RICHARDSON, M. A., IWAMOTO, A., IKEGAMI, N., NOMOTO, A., and FURUICHI, Y. (1984). Nucleotide sequence of the gene encoding the serotype-specific antigen of human (Wa) rotavirus: comparison with the homologous gene from simian SA11 and UK bovine rotaviruses. *J. Virol.* 51, 860–862.
78. RUIZ, A. M., LOPEZ, I. V., LOPEZ, S., ESPEJO, R. T., and ARIAS, C. F. Molecular and antigenic characterization of porcine rotavirus YM, a possible new rotavirus serotype. *J. Virol.* 162, 4331–4336, 1988.(12 X3)
79. RUSHLOW, K., MCNAB, A., OLSON, K., MAXWELL, F., MAXWELL, I., and STIEGLER, G. (1988). Nucleotide sequence of porcine rotavirus (OSU strain) gene segments 7, 8 and 9. *Nuc. Acids Res.* 16, 367–368.
80. Sambrook, J., Fritsch, E. F., and Maniatis, T., In "*Molecular cloning: A laboratory manual*", 2nd ed.,pp. 7.46–7.49. Cold Spring Harbor Laboratory Press, N.Y., 1989. (47 X3)
81. SANGER, F., NICKLEN, S., and COULSON, A. R. DNA sequencing with chain-terminating inhibitors. *Proc. Natl. Acad. Sci. USA* 74, 5463–5467, 1977.(27 X3)
82. SCHROEDER, B. A., STREET, J. E., KALMAKOFF, J., and BELLAMY, A. R. (1982). Sequence relationships between the genome segments of human and animal rotavirus strains. *J. Virol.* 43, 379–385.
83. Sippel, A. E., *Eur. J. Biochem.* 37, 31–40 (1973). (30 X3)
84. SMITH, E. M., ESTES, M. K., GRAHAM, D. Y., and GERBA, C. P. (1979). A plaque assay for the simian rotavirus SA11. *J. Gen. Virol.* 43, 513–519.(25 X3)
85. SNODGRASS, D. R., HOSHINO, Y., FITZGERALD, T. A., SMITH, M., BROWNING, G. F., and GORZIGLIA, M. Identification of four VP4 serological types (P serotypes) of bovine rotavirus using viral reassortants. *J. Gen. Virol.* 73, 2319–2325, 1992. (35 X3)
86. Snodgrass, D. R., Fitzgerald, T., Campbell, I., Scott, F. M. M., Browning, G. F., Miller, D. L., Herring, A. J., and Greenberg, H. B., *J. Clin. Microbiol.* 28, 504–507 (1990). (18 X3)
87. SOENARTO, Y., SEBODO, T., RIDHO, R., ALRASJID, H., ROHDE, J. E., BUGG, H. C., BARNES, G. L., and BISHOP, R. F. (1979). Acute diarrhea and rotavirus infection in newborn babies and children in Yogyakarta, Indonesia, from June 1978 to June 1979. *J. Clin. Microbiol.* 14, 123–129.
88. STEELE, A., GARCIA, D., SEARS, J., GERNA, G., NAKAGOMI, O., and FLORES, J. (1993). Distribution of VP4 gene alleles in human rotaviruses by using probes to the hyperdivergent region of the VP4 gene. *J. Clin. Microbiol.* 31, 1735–1740.
89. SUKUMARAN, M., GOWDA, K., MAIYA, P. P., SCRINIVAS, T. P., KUMAR, M. S., AIJAZ, S., REDDY, R. R., PADILLA, L., GREENBERG, H. B., and RAO, C. D. Exclusive asymptomatic neonatal infections by human rotavirus strains having subgoup I specificity and 'long' RNA electropherotype. *Arch. Virol.* 126, 239–251, 1992. (44 X3)
90. TANIGUCHI, K., NISHIKAWA, K., URASAWA, T., URASAWA, S., MIDTHUN, K., KAPIKIAN, A. Z., and GORZIGLIA, M. (1989). Complete nucleotide sequence of the gene encoding VP4 of a human rotavirus (strain K8) which has unique VP4 neutralization epitopes. *J. Virol.* 63, 4101–4106, 1989 (15 X3)9
91. TANIGUCHI, K., URASAWA, T., KOBAYSHI, N., GORZIGLIA, M., and URASAWA, S. (1990). Nucleotide sequence of VP4 and VP7 genes of human rotaviruses with subgroup I specificity and long RNA pattern: implication for new G serotype specificity. *J. Virol.* 64, 5640–5644.
92. TANIGUCHI, K., URASAWA, T., PONGSUWANNA, Y., CHOONTHANOM, M., JAYAVASU, C., and URASAWA, S. (1991). Molecular and antigenic analyses of serotypes 8 and 10 of bovine rotaviruses in Thailand. *J. Gen. Virol.* 72, 2929–2937.
93. Taniguchi K, Pongsuwanna Y, Choonthanon M, Urasawa S. Nucleotide sequence of the VP7 gene of a bovine rotavirus (strain 61A) with different serotype specificity from serotype 6. *Nuc Acids Res* 18:4613, 1990.(21 X1)
94. Taniguchi, K., Urasawa, T., Morita, Y., Greenberg, H. B., and Urasawa, S., *J. Infect. Dis.* 155, 1159–1166 (1987). (24 X3)
95. Taniguchi, K., Urasawa, S., and Urasawa, T., *J. Gen. Virol.* 66, 1045–1053 (1985). (29 X3)
96. URASAWA, S., URASAWA, T., WAKASUGI, F., KOBAYASHI, N., TANIGUCHI, K., LINTAG, I. C., SANIEL, M. C., and GOTO, H. Presumptive seventh serotype of human rotavirus. *Arch. Virol.* 113, 279–282, 1990.(17 X3)
97. Urasawa S, Hasegawa A, Urasawa T, et al. Antigenic and genetic analyses of human rotaviruses in Chiang Mai, Thailand: Evidence for a close relationship between human and animal rotaviruses. *J Infect Dis* 166:227–34, 1992.(19 X1, also X2)
98. WARD, R. L., NAKAGOMI, O., KNOWLTON, D. R., MCNEAL, M. M., NAKAGOMI, T., HUDA, N., CLEMENS, J. D., and SACK, D. A. (1991). Formation and selection of intergenogroup reassortants during cell culture adaptation of rotaviruses from dually infected subjects. *J. Virol.* 65, 2699–2701.
99. WHO. A manual for the treatment of diarrhoea, WHO/CDD/SER/80.2 Rev.2 (Programme for the Control of Diarrhoeal Diseases), 1990.(15 X1)
100. WYATT, R. G., GREENBERG, H. B., and JAMES, W. D. (1984). Definition of human rotavirus serotypes by plaque reduction assay. *Infect. Immun.* 37, 110–115.
101. XU, L., HARBOUR, D., and MCCRAE, M. A. (1991). Sequence of the gene encoding the major neutralization antigen (VP7) of serotype 10 rotavirus. *J. Gen. Virol.* 72, 177–180.
102. Jayashree A, Bhan MK, Bhandari N, Kumar R, Raj P, Sazawal S. Rotavirus-specific antibody response in saliva of infants with rotavirus diarrhea. *J Infect Dis* 162:1383–4, 1990.(12 X1)

What is claimed is:

1. An isolated rotavirus of strain G9P11 comprising a bovine VP4 virus gene and a human VP7 virus gene.

2. A rotavirus vaccine comprising the rotavirus of claim 1 in a pharmaceutically acceptable carrier.

3. The isolated rotavirus of claim 1, wherein the VP7 virus gene is substituted with the VP7 virus gene from strain G2P4.

4. The isolated rotavirus of claim 1, wherein the VP4 virus gene is substituted with the VP4 virus gene from strain G2P4.

* * * * *

UNITED STATES PATENT AND TRADEMARK OFFICE
CERTIFICATE OF CORRECTION

PATENT NO. : 5,773,009
DATED : 6/30/98
INVENTOR(S) : Glass et al.

It is certified that error appears in the above-identified patent and that said Letters Patent is hereby corrected as shown below:

Column 3, line 21, after "substitutions." insert --Virus isolate 116E was deposited on September 2, 1997, with the American Type Culture Collection, 12301 Parklawn Drive, Rockville, Md. 20852, under accession number VR 2590.--

Signed and Sealed this

Sixteenth Day of February, 1999

Attest:

Attesting Officer

*Acting Commissioner of Patents and Trademarks*